United States Patent

Tadanier et al.

[11] 4,173,564
[45] Nov. 6, 1979

[54] 4-N-ACYLFORTIMICIN B DERIVATIVES AND THE CHEMICAL CONVERSION OF FORTIMICIN B TO FORTIMICIN A

[75] Inventors: John S. Tadanier; Jerry R. Martin; Paul Kurath, all of Waukegan, Ill.

[73] Assignee: Abbott Laboratories, North Chicago, Ill.

[21] Appl. No.: 956,751

[22] Filed: Nov. 1, 1978

Related U.S. Application Data

[62] Division of Ser. No. 888,085, Mar. 20, 1978, which is a division of Ser. No. 725,829, Sep. 23, 1976, Pat. No. 4,091,032.

[51] Int. Cl.$^2$ .................. C07C 103/52; C07D 309/22; A61K 37/00
[52] U.S. Cl. ...................... 260/112.5 R; 260/345.9 R; 424/177
[58] Field of Search ................. 260/112.5 R, 345.9 R; 424/177

[56] References Cited

U.S. PATENT DOCUMENTS 3,931,400  1/1976  Nara et al. .......................... 195/80 R

*Primary Examiner*—Delbert R. Phillips
*Attorney, Agent, or Firm*—Robert L. Niblack; Gildo E. Fato

[57] ABSTRACT

This invention provides 4-N-acylfortimicin B derivatives of the structure

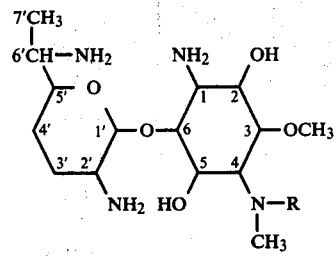

wherein R is acyl, aminoacyl, N-monoloweralkylaminoacyl, N,N-diloweralkylaminoacyl, hydroxy-substituted aminoacyl, or substituted aminoacyl of the formula

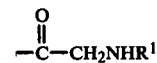

where $R^1$ is an acyl radical derived from an amino acid or a short peptide, and the pharmaceutically acceptable salts thereof.

The compounds are useful as intermediates for preparing 4-N-alkyl or substituted alkylfortimicin B derivatives. In addition to their utility as intermediates, some of the compounds of this invention are also useful as antimicrobial agents.

17 Claims, No Drawings

4-N-ACYLFORTIMICIN B DERIVATIVES AND THE CHEMICAL CONVERSION OF FORTIMICIN B TO FORTIMICIN A

This is a division, of application Ser. No. 888,085, filed Mar. 20, 1978, which is a division of application Ser. No. 725,829, filed Sept. 23, 1976, now U.S. Pat. No. 4,091,032, issued May 23, 1978.

BACKGROUND OF THE INVENTION

Antibiotic therapy plays a vital role in modern medicine. The advent of antibiotic therapy in this century has, in part, been responsible for the increased life expectancy, as well as lower instances of infant and childbirth deaths. While there are numerous classes of antibiotics available, the semi-synthetic penicillins, the tetracyclines, erythromycins and cephalosporins are probably the most widely used antibiotics.

Despite the availability of a variety of highly effective antibiotics, the search for improved agents is a continuing one for a variety of reasons. Many organisms become resistant to a particular antibiotic or class of antibiotics and thus new drug entities must be continually made available to treat infections involving strains of organisms which have become resistant to all other therapy. Apart from the problem of resistance, this powerful class of drugs have a number of undesirable side effects and thus the search continues for agents which are lower in toxicity than presently available antibiotics yet are effective antimicrobial agents.

Another problem with current antibiotic therapy is that there are certain organisms, such as the genus proteus of organisms, which are very difficult to treat. Thus researchers are constantly seeking new entities which would be effective against various proteus strains.

Recently a new class of antibiotics has been identified and designated as the fortimicins. To date, two fortimicin antibiotics are known, fortimicin A and fortimicin B. Both antibiotics are fermentation products and thus are difficult and expensive to manufacture.

Fortimicin A exhibits a wide range of in vitro activity against gram-positive and gram-negative bacteria and also exhibits excellent activity against strains of *Staphylococcus aureus* and *Escherichia coli* which is resistant to various known antibiotics such as kanamycin, gentamicin, tobramycin and the like, as well as exhibiting antibacterial activity against bacteria of the genus Proteus. In vivo tests indicate the $ED_{50}$ of fortimicin A against *Escherichia coli* Juhl KY 4286 in mice to be 6 mg./kg. (See U.S. Pat. No. 3,976,768).

Fortimicin B also exhibits in vitro antibacterial activity against various gram-positive and gram-negative antibiotics, but is considerably less active than fortimicin A. (See U.S. Pat. No. 3,931,400.)

While fortimicin A is a promising lead in the class of fortimicin antibiotics, it has been found that the 4-N-alkylfortimicin B derivatives are generally more stable, but just as effective as fortimicin A.

The present invention provides a novel series of intermediates which are useful in preparing the 4-N-alkylfortimicin derivatives and also provides a method of converting fortimicin B to fortimicin A.

SUMMARY OF THE INVENTION

This invention provides a novel series of 4-N-acylfortimicin B derivatives which are useful as intermediates in the synthesis of 4-N-alkylfortimicin B derivatives. In addition to their utility as intermediates, some of the compounds of this invention, as shown in Table II are also useful as antimicrobial agents.

This invention also provides a method for the chemical conversion of the less active fortimicin B to fortimicin A, as well as 4-N-acylfortimicin B derivatives.

Generally speaking the 4-N-alkylfortimicin B derivatives are prepared by reducing the acyl amide function of the particular 4-N-acylfortimicin B derivative with for example lithium aluminum hydride or diborane which are standard amide reduction procedures. The compounds of this invention are used as intermediates in the synthesis of 4-N-substituted alkylfortimicin B derivatives as well as 4-N-alkylfortimicin B derivatives. Specifically, in addition to the 4-N-alkyl derivatives, they are useful in preparing 4-N-aminoalkyl or 4-N-hydroxyalkyl derivatives of fortimicin B.

The present invention also provides for the chemical conversion of fortimicin B (1) of the formula

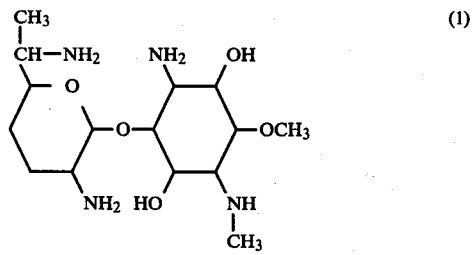

(1)

to fortimicin A (2) of the formula

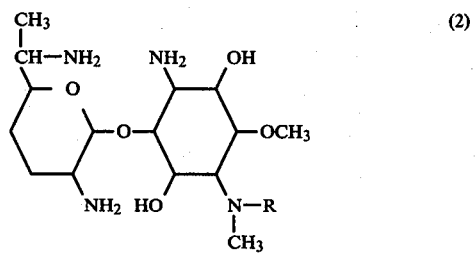

(2)

where R is

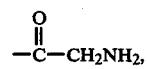

and the preparation of fortimicin A analogs (4-N-acylfortimicin B derivatives) in which the 4-N-glycyl group of the naturally occurring aminocyclitol antibiotic, fortimicin A (2), is replaced by acyl groups derived from carboxylic acids and amino acids other than glycine where R is as defined above. In particular, the invention is concerned with the preparation of 4-N-acylfortimicin B derivatives in which the 4-N-acyl group is derived from an amino acid or a peptide, and their pharmaceutically acceptable salts.

DETAILED DESCRIPTION OF THE INVENTION

This invention is related to novel fortimicins and more particularly to 4-N-acylfortimicin B derivatives, and to the chemical conversion of fortimicin B to fortimicin A. The compounds of the present invention are represented by the formula

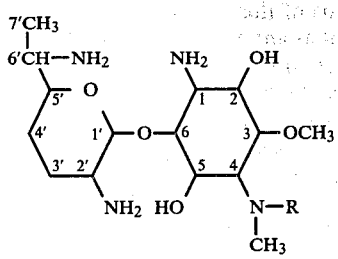

wherein R is acyl, aminoacyl, N-monoloweralkylaminoacyl, N,N-diloweralkylaminoacyl, hydroxy-substituted aminoacyl, or substituted aminoacyl of the formula

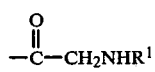

where $R^1$ is an acyl radical derived from an amino acid or a short peptide, and the pharmaceutically acceptable salts thereof.

These compounds are useful as intermediates for preparing 4-N-alkyl or substituted alkylfortimicin B derivatives. In addition to the utilities as intermediates, some of the compounds of this invention are also useful as antimicrobial agents.

The term "acyl" as used herein, refers to groups R represented by the formula

wherein $R^2$ is loweralkyl, aminoloweralkyl, N-substituted-aminoloweralkyl and N,N-disubstituted-aminoloweralkyl wherein the N-substituents of the N-substituted-aminoloweralkyl and N,N-disubstituted-aminoloweralkyl groups are comprised of alkyl groups such as methyl and ethyl. The term "lower alkyl" refers to both straight and branched chain $C_1$–$C_7$ alkyl groups.

In addition, the term "acyl" as used herein, refers to groups R represented by the formula

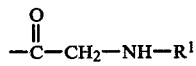

wherein $R^1$ is an acyl radical derived from an amino acid or a short peptide.

In addition, the acyl groups are derived from naturally occurring amino acids of their enantiomers, which are not included among those defined above, such as histidine, phenylalanine, tyrosine, or small peptides such as glycylglycine or other di- or tri-peptides.

As used herein, the term "Cbz" refers to benzyloxycarbonyl.

The term "pharmaceutically acceptable salts," as used herein, refers to the non-toxic acid addition salts which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate and the like.

The method illustrated below, which may be used for the preparation of fortimicin A (2) from fortimicin B (1) and also for the preparation of the fortimicin A analogs (5) involves as the first step the preparation of 1,2',6'-tri-N-benzyloxycarbonylfortimicin B (3) by treatment of fortimicin B (1) with a suitable acylating agent such as N-(benzyloxycarbonyloxy) succinimide (6), benzyloxycarbonyl-p-nitrophenol (8), respectively.

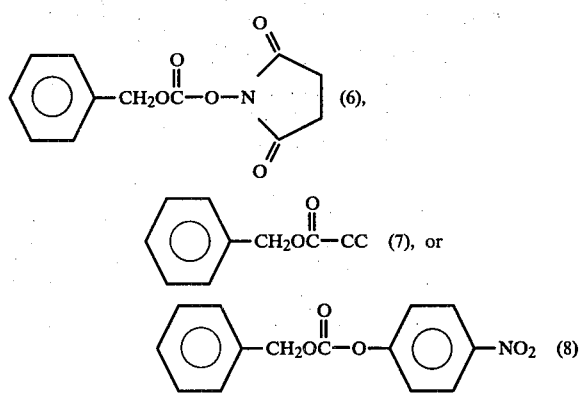

in a solvent such as N,N-dimethylformamide, methanol-water, and the like according to Scheme 1:

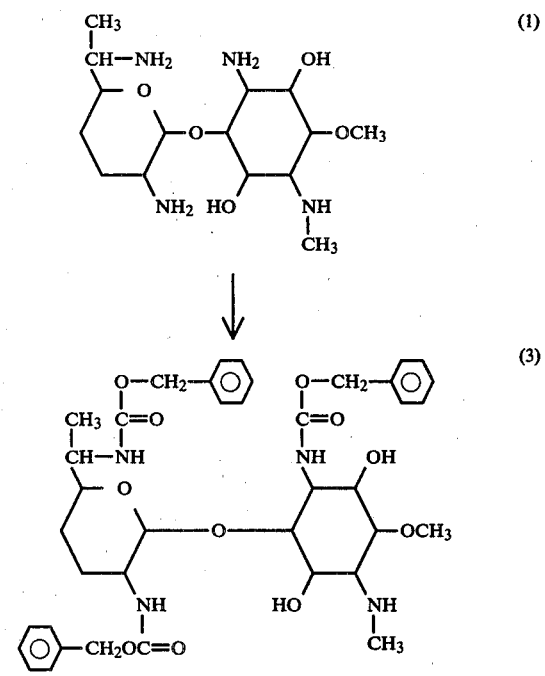

SCHEME 1

The second step of the process, the acylation of the C4-N-methylamino group of 1,2',6'-tri-N-benzyloxycarbonylfortimicin B (3) is accomplished with an activated carboxylic acid derivative such as carboxylic acid anhydride, a carboxylic acid chloride, an active carboxylic acid ester, or a carboxylic acid azide following the methodology commonly used in peptide synthesis.

The active esters may be prepared from the carboxylic acid derivative

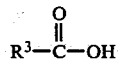

with 1-hydroxybenzotriazole, N-hydroxysuccinimide, or N-hydroxy-5-norbornene-2,3-dicarboximide [M. Fujino, S. Kobayashi, M. Obayashi, T. Fukuda, S. Shinagawa, and O. Nishimura, Chem. Pharm. Bull. Japan, 22, 1857 (1974)] respectively, as illustrated in Schemes A, B and C, below, wherein

is acyl, N,N-diloweralkylaminoacyl, or an acyl group derived from an N-benzyloxycarbonyl protected amino acid or a short peptide.

Scheme A

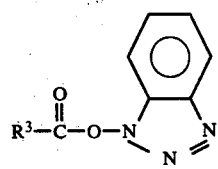
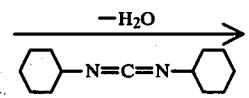
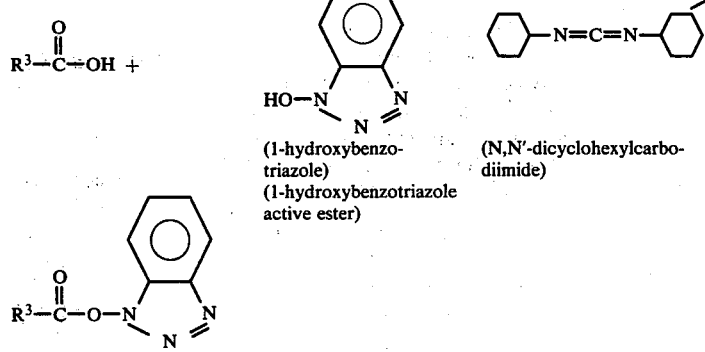

Scheme B

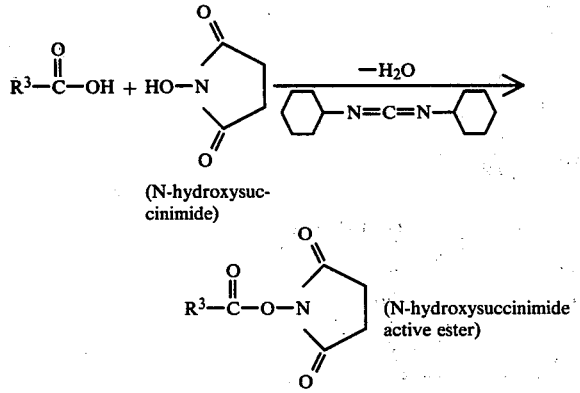

Scheme C

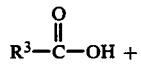
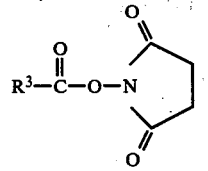

-continued
Scheme C

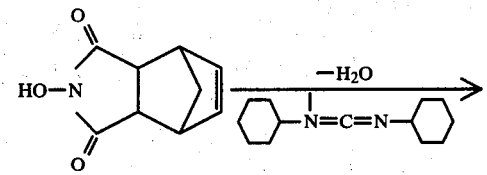
(N-hydroxy-5-nor-bornene-2,3-di-carboximide)

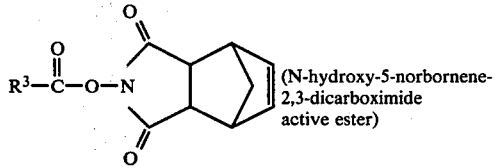
(N-hydroxy-5-norbornene-2,3-dicarboximide active ester)

The reactions of the active esters with 1,2',6'-tri-N-benzyloxycarbonylfortimicin B (3) are carried out in an inert solvent such as tetrahydrofuran, dioxane, chloroform, N,N-dimethyl-formamide and the like. In some cases, the addition of a tertiary amine, such as triethylamine, proves beneficial.

In some of the couplings, the azide group is used to activate the carboxyl terminal of the carboxylic acid to be coupled. The acyl azides are made from the corresponding acyl hydrazides with HNO$_2$ (nitrous acid), and the excess acid is removed by a basic aqueous wash. The reaction is illustrated below:

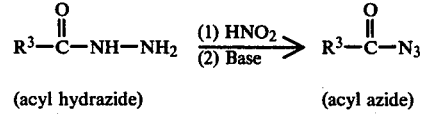

(acyl hydrazide)         (acyl azide)

where

represents the same groups as in the active ester preparation above. The coupling reactions of the acyl azides prepared above with 1,2',6'-tri-N-benzyloxycarbonyl-fortimicin B (3) are carried out in an inert solvent such as ethyl acetate.

The coupling reactions of the above N-protected carboxyl activated derivatives at the C$_4$-N-methyl group of 1,2′,6′-tri-N-benzyloxycarbonylfortimicin B (3) to form 4-N-acyl-1,2′,6′-tri-N-benzyloxycarbonyl-fortimicin B (4) is illustrated in Scheme 2 below:

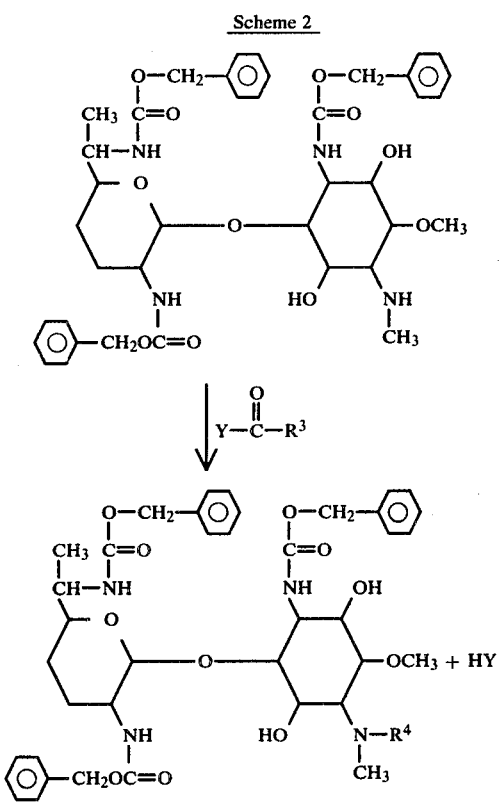

where Y represents activating groups such as:

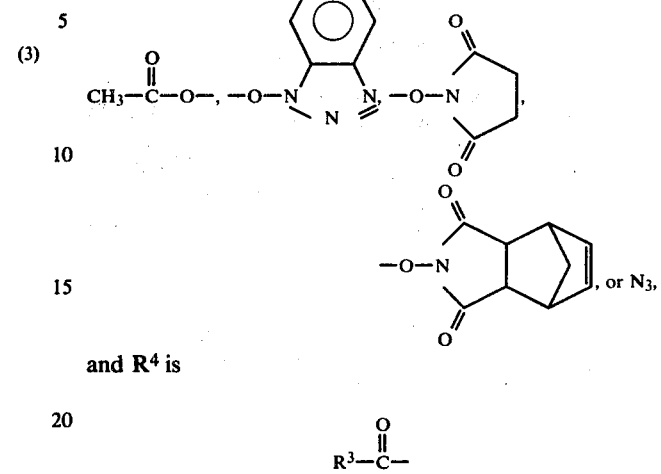

and $R^4$ is $$R^3-\overset{O}{\underset{\|}{C}}-$$

as defined above.

To those skilled in the art of peptide synthesis it is obvious that the introduction of a short N-protected peptide chain in 3 to afford 4 may be achieved in a stepwise manner by using suitably protected intermediates as illustrated in Scheme 3 below:

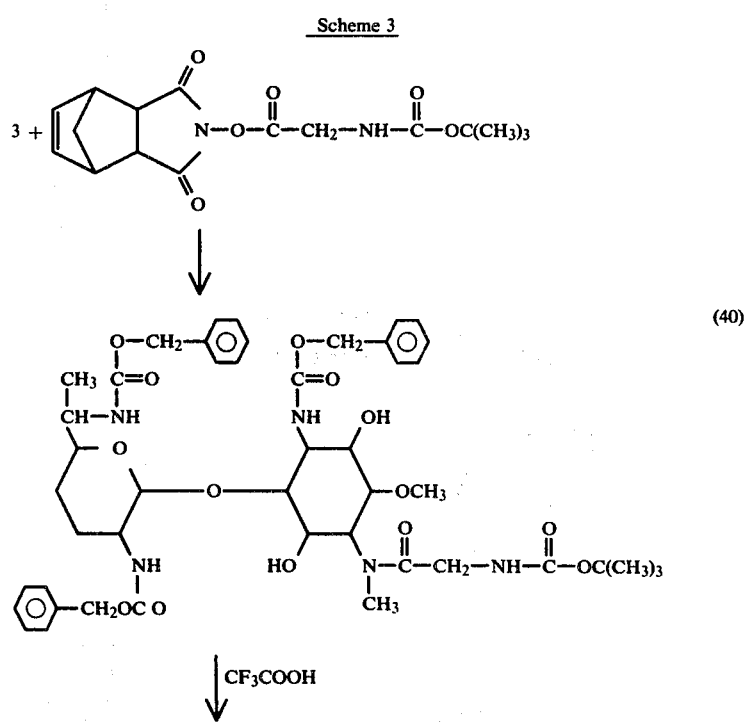

Scheme 3

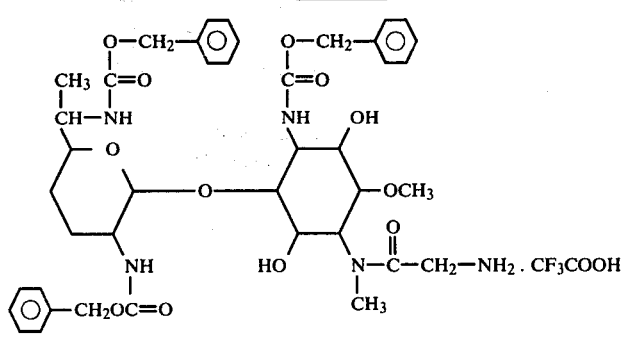
(41)

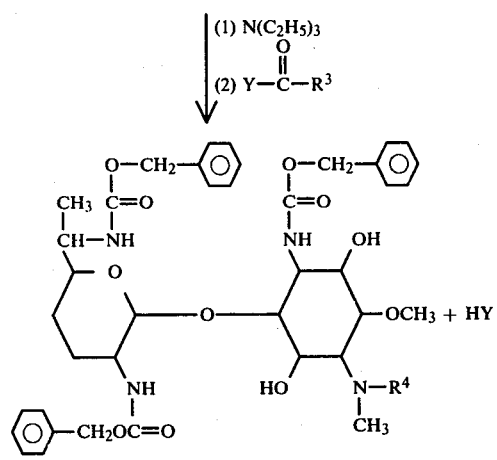
(4)

wherein R⁴ is

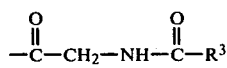

where

is as defined earlier and Y is an activating group as defined above.

The stepwise synthesis proceeds via 4-N-(N-tert-butyloxycarbonylglycyl)-1,2',6'-tri-N-benzyloxycarbonylfortimicin B (40) which under acidic conditions, such as trifluoroacetic acid in methylene chloride, gives rise to 4-N-glycyl-1,2',6'-tri-N-benzyloxycarbonylfortimicin B trifluoroacetate salt (41). The latter (41) is first treated with triethylamine and then allowed to react in the usual manner with

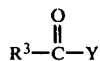

to yield the 4-N-acyl-1,2',6'-tri-N-benzyloxycarbonylfortimicin B (4) intermediates in a stepwise procedure.

After completion of the acylation at the C₄-N-methyl group of 1,2',6'-tri-N-benzyloxycarbonylfortimicin B (3) to form the protected intermediates 4, it is necessary to remove the benzyloxycarbonyl protecting groups of 4 by hydrogenolysis of the latter (4) over a palladium on carbon catalyst to obtain the biologically active fortimicin A analogs (5). Fortimicin A (2) and the fortimicin A analogs (5) thus prepared are conveniently isolated as the hydrochloride salts when the hydrogenolyses are carried out in the presence of a slight excess of hydrochloric acid. The hydrogenolyses of 4 to obtain 5 are formulated in Scheme 4 below:

Scheme 4

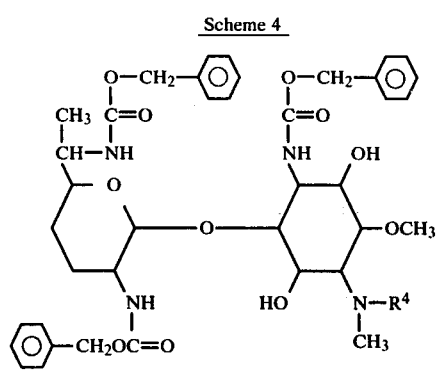
(4)

-continued
Scheme 4

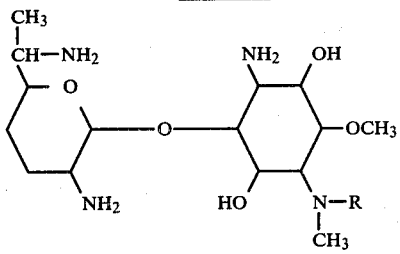
(5)

wherein R⁴ and R are as defined above.

The compounds which may be prepared according to the method described above include the compounds represented by the formula

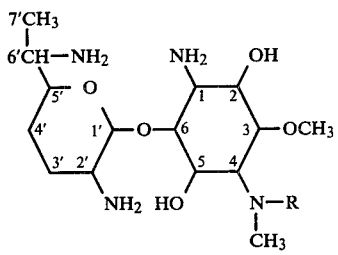

where R is as defined above. Examples of such compounds, which are not meant to limit the scope of the invention, are the following:

(9) the tetrahydrochloride salt of fortimicin A, where R is

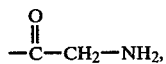
—C—CH₂—NH₂,

(10) the tetrahydrochloride salt of 4-N-(DL-2-hydroxy-4-aminobutyryl)fortimicin B where R is

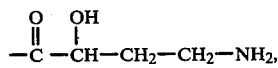

(11) the trihydrochloride salt of 4-N-acetylfortimicin B where R is

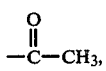

(12) the tetrahydrochloride salt of 4-N-glyclglycyl-fortimicin B where R is

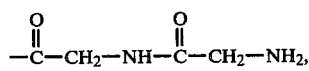

(13) the tetrahydrochloride salt of 4-N-sarcosylfortimicin B where R is

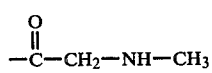

(14) the tetrahydrochloride salt of 4-N-L-phenylalanylglycylfortimicin B where R is

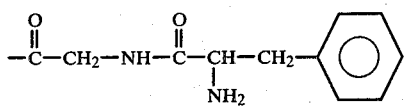

(15) the tetrahydrochloride salt of 4-N-(N,N-dinethylglycyl)fortimicin B where R is

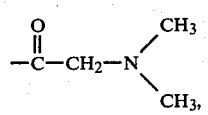

(16) the tetrahydrochloride salt of 4-N-β-alanylfortimicin B where R is

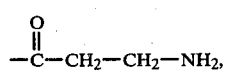

(17) the tetrahydrochloride salt of 4-N-D-alanylfortimicin B where R is

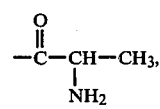

(18) the tetrahydrochloride salt of 4-N-L-alanylfortimicin B where R is

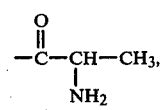

(19) the tetrahydrochloride salt of 4-N-L-alanylglycylfortimicin B where R is

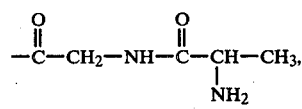

(20) the tetrahydrochloride salt of 4-N-L-leucylglycylfortimicin B where R is

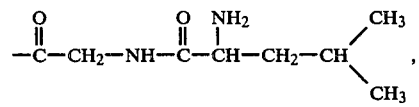

(21) the tetrahydrochloride salt of 4-N-(DL-2-hydroxy-4-aminobutyryl)glycylfortimicin B where R is

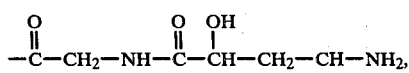

(22) the pentahydrochloride salt of 4-N-L-histidylfortimicin B where R is

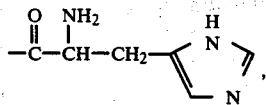

(23) the tetrahydrochloride salt of 4-N-glycylglycylglycylfortimicin B where R is

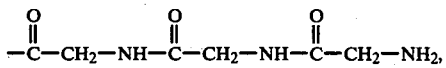

(24) the tetrahydrochloride salt of 4-N-(DL-2-hydroxy-3-aminopropionyl)glycylfortimicin B where R is

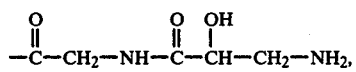

(25) the tetrahydrochloride salt of 4-N-(DL-2-hydroxy-3-aminopropionyl)fortimicin B where R is

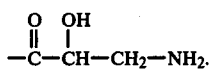

The following examples are provided to further illustrate the present invention and are not intended to limit or restrict the invention.

EXAMPLE 1

1,2',6'-Tri-N-benzyloxycarbonylfortimicin B (3)

To a stirred solution of 2.0 g. of fortimicin B (1), 30 ml. of water, and 60 ml. of methanol, cooled in an ice bath at 0°, was added 4.44 g. of N-(benzyloxycarbonyloxy)succinimide. Stirring was continued at 0° for 3 hours and then at ambient temperature for 22 hours. The major portion of the methanol was evaporated under reduced pressure and the residue was shaken with a mixture of chloroform and water. The chloroform solution was washed with water and dried over anhydrous magnesium sulfate. The chloroform was evaporated and the residue was chromatographed on silica gel. Elution with a solvent system composed of chloroform-methanol-concentrated ammonium hydroxide (23.4:1.4:0.1 v/v) yielded 1.05 g. of 1,2',6'-tri-N-benzyloxycarbonylfortimicin B (3): $[\alpha]_D^{25}+16.5°$ (C 1.0, CH$_3$OH); IR 1712, 1507 cm$^{-1}$; NMR (CDCl$_3$) δ 1.03 (C$_6'$-CH$_3$, J=6.0), 2.32 (NHCH$_3$), 3.41 (OCH$_3$).

Analysis Calcd. for: C$_{39}$H$_{50}$N$_4$O$_{11}$: C, 62.39; H, 6.71; N, 7.46 Found: C, 62.16; H, 6.76; N, 7.43

EXAMPLE 2

Tetra-N-benzyloxycarbonylfortimicin A (26)

A. To a magnetically stirred solution of 1.00 g. of 1,2',6'-tri-N-benzyloxycarbonylfortimicin B (3), 0.357 g. of N-benzyloxycarbonylglycine and 0.376 g. of 1-hydroxybenzotriazole monohydrate in 2.8 ml. of tetrahydrofuran, cooled to 0° in an ice bath, was added a solution of 0.353 g. of N,N'-dicyclohexylcarbodiimide in 2.8 ml. of tetrahydrofuran. An additional 2.8 ml. of tetrahydrofuran was added to rinse all the N,N-dicyclohexylcarbodiimide into the reaction vessel. Stirring was continued at 0° for 1 hour and then at ambient temperature for 18 hours. The precipitated N,N'-dicyclohexylurea was removed by filtration. The tetrahydrofuran was evaporated from the filtrate under reduced pressure leaving 1.79 g. of product. A sample (1.20 g.) was chromatographed on a column of silica gel, prepared and eluted with a solvent system consisting of benzene-methanol-95% ethanol-concentrated ammonium hydroxide (23.5:1.4:2.0:0.2 v/v). Fractions containing the desired product were combined and concentrated under reduced pressure leaving 0.826 g. of tetra-N-benzyloxycarbonylfortimicin A: $[\alpha]_D^{23}+52.9°$ (C 1.0, CH$_3$OH); IR 1710, 1635, 1500 cm$^{-1}$; NMR (CDCl$_3$) δ 1.16 (C$_6'$-CH$_3$, J=6.5), 2.82 (C$_4$-NCH$_3$), 3.31 (OCH$_3$), 4.80 (H$_1'$, J=3.0).

Analysis Calcd: for: C$_{49}$H$_{59}$N$_5$O$_{14}$: C, 62.48; H, 6.31; N, 7.43 Found: C, 62.52; H, 6.49; N, 7.23

B. To a magnetically stirred solution of 4.02 g. of 1,2',6'-tri-N-benzyloxycarbonylfortimicin B in 40 ml. of tetrahydrofuran, cooled to 0° in an ice bath, was added 1.80 g. of the N-hydroxysuccinimide ester of N-benzyloxycarbonylglycine. Stirring was continued at 0° for 4 hours and then at room temperature for 23 hours. The resulting solution was shaken with a mixture of 300 ml. of CHCl$_3$ and 400 ml. of 5% aqueous NaHCO$_3$ solution. The CHCl$_3$ solution was separated and washed with 400 ml. of water. The aqueous solutions were washed in series with three 200 ml. portions of CHCl$_3$. The CHCl$_3$ was evaporated under reduced pressure to yield 5.18 g. of a white glass. This product was chromatographed on a column of 250 g. of silica gel (3.4×74 cm.). Elution was carried out with a solvent system composed of benzene-methanol-ethanol-ammonium hydroxide (23.5:1.60:1.80:0.20 v/v). The fractions containing the product were combined, and evaporation of the solvent left 4.58 g. of tetra-N-benzyloxycarbonylfortimicin A (26) identical with that prepared as described above.

EXAMPLE 3

Tetra-N-benzyloxycarbonyl-4-N-(DL-2-hydroxy-4-aminobutyryl)fortimicin B (27)

To a magnetically stirred solution of 1.03 g. of 1,2',6'-tri-N-benzyloxycarbonylfortimicin B (3), 0.693 g. of N-benzyloxycarbonyl-DL-1-hydroxy-4-aminobutyric acid, and 0.829 g. of 1-hydroxybenzotriazole monohydrate in 5 ml. of tetrahydrofuran, cooled in an ice bath, was added a solution of 0.560 g. of N,N'-dicyclohexylcarbodiimide in 2.5 ml. of tetrahydrofuran. An additional 2.5 ml. of tetrahydrofuran was added to rinse all of the N,N'-dicyclohexylcarbodiimide into the reaction vessel. Stirring was continued for 15 minutes in the ice bath and 0.8 ml. of triethylamine was then added. Stirring was continued at 0° for 15 minutes and then at ambient temperature for 21.5 hours. Insoluble N,N-dicyclohexylurea was separated by filtration and the tetrahydrofuran was removed from the filtrate leaving 2.91 g. of a yellow glass. Chromatography was carried out first on a silica gel column by eluting with a solvent system composed of benzene-methanol-ethanol-concentrated ammonium hydroxide (23.5:0.7:2.7:0.2 v/v). Fractions enriched in the desired product were combined and rechromatographed on silica gel using a solvent system composed of benzene-methanol-ethanol (23.5:0.7:2.7 v/v). Fractions enriched in the desired product were then chromatographed on Sephadex LH-20 in methanol to yield 0.353 g. of tetra-N-benzyloxycarbonyl-4-N-(DL-2-hydroxy-4-aminobutyryl)fortimicin B (27): $[\alpha]_D^{24}+42.4°$ (C 1.0, CH$_3$OH); IR 1705, 1623, 1504 cm$^{-1}$; NMR (CDCl$_3$) δ 1.19 (C$_6$'-CH$_3$), 2.9 (C$_4$-NCH$_3$), 3.32 (OCH$_3$), 4.75 (H$_1$', J=3.0).

Analysis Calcd. for: C$_{51}$H$_{63}$N$_5$O$_{15}$: C, 62.12; H, 6.44; N, 7.10 Found: C, 62.07; H, 6.54; N, 7.07

EXAMPLE 4

1,2',6'-Tri-N-benzyloxycarbonyl-4-N-acetylfortimicin B (28)

To a stirred solution of 3.22 g. of 1,2',6'-tri-N-benzyloxycarbonylfortimicin B (3) in 225 ml. of methanol, cooled in an ice bath, was added 16 ml. of acetic anhydride over a period of 15 minutes. Stirring was continued at 0° for 2 hours and then at room temperature for 2 hours. The methanol was evaporated under reduced pressure and residual acetic anhydride and acetic acid were removed by co-distillation with benzene and methanol to leave 3.63 g. of 1,2',6'-tri-N-benzyloxycarbonyl-4-N-acetylfortimicin B (28): $[\alpha]_D^{25}$+58.4° (C 1.03, CH$_3$OH); IR 1710, 1620, 1500 cm$^{-1}$; NMR (CDCl$_3$) δ 1.16 (C$_6$'-CH$_3$, J=6.0), 2.07 (COCH$_3$), 2.83 (C$_4$-NCH$_3$), 3.34 (OCH$_3$), 4.81 (H$_1$', J=3.0).

Analysis Calcd. for: C$_{41}$H$_{52}$N$_4$O$_{12}$: C, 62.11; H, 6.61; N, 7.07 Found: C, 62.37; H, 6.74; N, 7.00

EXAMPLE 5

Tetra-N-benzyloxycarbonyl-4-N-glycylglycylfortimicin B (29)

To a stirred suspension of 0.754 g. of 1,2'-6'-tri-N-benzyloxycarbonylfortimicin B (3), 0.536 g. of N-benzyloxycarbonylglycylglycine and 0.622 g. of 1-hydroxybenzotriazole monohydrate in 4 ml. of tetrahydrofuran was added a solution of 0.418 g. of N,N'-dicyclohexylcarbodiimide in 3 ml. of tetrahydrofuran. An additional 3 ml. of tetrahydrofuran was used to rinse all of the N,N'-dicyclohexylcarbodiimide into the reaction vessel. The resulting suspension was stirred at room temperature for 44 hours. The insoluble N,N'-dicyclohexylurea was then removed by filtration and washed thoroughly with tetrahydrofuran. The filtrate and washings were combined, and the tetrahydrofuran was evaporated under reduced pressure leaving 1.96 g. of a white glass. The product was chromatographed on a column of silica gel. Elution with a solvent system composed of benzene-methanol-ethanol-concentrated ammonium hydroxide (23.5:0.7:2.7:0.2 v/v) yielded 0.824 g. of tetra-N-benzyloxycarbonyl-4-N-glycylglycylfortimicin B (20): $[\alpha]_D^{23}$+43° (C 1.0, CH$_3$OH); IR 1712, 1638, 1500 cm$^{-1}$; NMR (CDCl$_3$) δ 1.17 (C$_6$'—CH$_3$, J=6), 2.87 (C$_4$-NCH$_3$) 3.32 (OCH$_3$).

Analysis Calcd. for: C$_{51}$H$_{62}$N$_6$O$_{15}$: C, 61.31; H, 6.25; N, 8.41 Found: C, 61.35; H, 6.40; N, 8.28

EXAMPLE 6

Tetra-N-benzyloxycarbonyl-4-N-sarcosylfortimicin B (30)

To a stirred solution of 2.26 g. of 1,2',6'-tri-N-benzyloxycarbonylfortimicin B (3), 0.855 g. of N-benzyloxycarbonylsarcosine and 0.982 g. of 1-hydroxybenzotriazole monohydrate in 12.0 ml. of tetrahydrofuran was added 0.808 g. of N,N'-dicyclohexylcarbodiimide dissolved in 6.0 ml. of tetrahydrofuran. An additional 6.0 ml. of tetrahydrofuran was used to rinse all the N,N'-dicyclohexylcarbodiimide into the reaction vessel. Stirring was continued for 24 hours at room temperature. Insoluble N,N'-dicyclohexylurea was removed by filtration with a sintered glass funnel. Removal of the tetrahydrofuran under reduced pressure gave a yellow residue which was chromatographed on a column of silica gel prepared and eluted with a solvent system consisting of benzene-methanol-95% ethanol-concentrated ammonium hydroxide (23.5:1.4:2.0:0.2 v/v). Fractions enriched in tetra-N-benzyloxycarbonyl-4-N-sarcosylfortimicin B (30) were collected and rechromatographed on a column of Sephadex LH-20 prepared and eluted with 95% ethanol. Appropriate fractions were combined to give 2.29 g. of tetra-N-benzyloxycarbonyl-4-N-sarcosylfortimicin B (30) as a white foam: $[\alpha]_D^{24}$+49.9° (C 1.0, CH$_3$OH); IR 1710, 1635, 1500 cm$^{-1}$; NMR (CDCl$_3$) δ 1.15 (C$_6$'-CH$_3$, J=6.8), 2.79 (C$_4$-NCH$_3$), 2.98 (OCH$_3$), 3.35

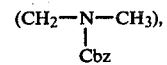

4.82 (H$_1$', J=3.0).

Analysis Calcd. for: C$_{50}$H$_{61}$N$_5$O$_{14}$: C, 62.82; H, 6.43; N, 7.32 Found: C, 62.59; H, 6.47; N, 7.32

EXAMPLE 7

Tetra-N-benzyloxycarbonyl-4-N-L-phenylalanylglycylfortimicin B (31)

To a stirred solution of 2.00 g. of 1,2',6'-tri-N-benzyloxycarbonylfortimicin B (3), 1.284 g. of N-benzyloxycarbonyl-L-phenylalanylglycine and 0.892 g. of 1-hydroxybenzotriazole monohydrate in 10 ml. of tetrahydrofuran was added 0.602 g. of N,N'-dicyclohexylcarbodiimide dissolved in 5.0 ml. of tetrahydrofuran. An additional 5.0 ml. of tetrahydrofuran was used to rinse all the N,N'-dicyclohexylcarbodiimide into the reaction vessel. Stirring was continued for 20 hours at room temperature. Insoluble dicyclohexylurea was removed by filtration through a sintered glass funnel. The filtrate was concentrated to dryness to leave a yellow residue. The residue was chromatographed on a column of silica gel prepared and eluted with a solvent system composed of benzene-methanol-95% ethanol-concentrated ammonium hydroxide (23.5:1.4:2.0:0.2 v/v). Fractions enriched in the desired component were collected and evaporated to dryness. The residue was passed through a column of Sephadex LH-20 prepared and eluted with 95% ethanol. Fractions containing pure tetra-N-benzyloxycarbonyl-4-N-L-phenylalanylglycylfortimicin B (31) were collected and the ethanol was evaporated under reduced pressure to give 1.16 g. of product: $[\alpha]_D^{25}$+28.4° (C 1.03, CH$_3$OH); IR 1712, 1637, 1500 cm$^{-1}$; NMR (CDCl$_3$) δ 1.16 (C$_6$'-CH$_3$, J=6), 2.80 (C$_4$-NCH$_3$), 3.27 (OCH$_3$).

Analysis Calcd. for: C$_{58}$H$_{68}$N$_6$O$_{15}$: C, 63.96; H, 6.29; N, 7.72 Found: C, 63.82; H, 6.45; N, 7.71

EXAMPLE 8

1,2',6'-Tri-N-benzyloxycarbonyl-(N,N-dimethylglycyl)fortimicin B (32)

To a stirred solution of 2.26 g. of 1,2',6'-tri-N-benzyloxycarbonylfortimicin B (3), 0.515 g. of dimethylglycine and 1.03 g. of 1-hydroxybenzotriazole monohydrate in 6.0 ml. of tetrahydrofuran was added 0.840 g. of N,N'-dicyclohexylcarbodiimide dissolved in 6.0 ml of tetrahydrofuran. An additional 6.0 ml. of tetrahydrofuran was used to rinse all the N,N'-dicyclohexylcarbodiimide into the reaction vessel. Triethylamine (1.5 ml.) was added to the reaction mixture and stirring was continued for 20 hours at ambient temperature. Insoluble dicyclohexylurea was removed by filtration through a sintered glass funnel and the filtrate was taken to dryness. The residue was chromatographed on a column of silica gel prepared and eluted with a solvent system composed of methylene chloride-95% aqueous methanol-concentrated ammonium hydroxide (18.2:1.8:0.2 v/v). Fractions containing pure 1,2′,6′-tri-N-benzyloxycarbonyl-(N,N-dimethylglycyl)fortimicin B (32) were collected and evaporated to dryness to give 1.34 g. of a colorless glass: $[\alpha]_D^{23}+46.1°$ (C 1.0, CH$_3$OH); IR 1711, 1630, 1503 cm$^{-1}$; NMR (CDCl$_3$) δ 1.16 (C$_6$′-CH$_3$, J=6), 2.3 [N(CH$_3$)$_2$], 2.89 (C$_4$-NCH$_3$), 3.06 (COCH$_2$-N<), 3.34 (OCH$_3$), 4.82 (H$_1$′, J=3.0).

Analysis Calcd. for: C$_{43}$H$_{57}$N$_5$O$_{12}$: C, 61.78; H, 6.87; N, 8.38 Found: C, 61.75; H, 7.02; N, 8.30

EXAMPLE 9

Tetra-N-benzyloxycarbonyl-4-N-β-alanylfortimicin B (33)

To a stirred solution of 5.52 g. of 1,2′,6′-tri-N-benzyloxycarbonyl-β-alanine and 1.96 g. of 1-hydroxybenzotriazole monohydrate in 24.0 ml. of tetrahydrofuran was was added 1.62 g. of N,N′-dicyclohexylcarbodiimide dissolved in 12.0 ml. of tetrahydrofuran. An additional 12.0 ml. of tetrahydrofuran was used to rinse all the N,N′-dicyclohexylcarbodiimide into the reaction vessel. Stirring was continued for 20 hours at room temperature. Insoluble dicyclohexylurea was removed by filtration through a sintered glass funnel. The filtrate was concentrated to dryness under reduced pressure to yield 8.79 g. of a yellow glass. The glass was chromatographed on a column of silica gel using a solvent system of benzene-methanol-95% ethanol-concentrated ammonium hydroxide (23.5:1.4:2.0:0.2 v/v). Fractions enriched in the desired product were collected, taken to dryness and rechromatographed on a column of Sephadex LH-20 prepared in 95% ethanol. Elution with the same solvent gave fractions containing the desired product. Removal of the ethanol under reduced pressure gave 4.76 g. of tetra-N-benzyloxycarbonyl-4-N-β-alanylfortimicin B (33) as a white glass: $[\alpha]_D^{23}+42.9°$ (C 0.94, CH$_3$OH); IR 1710, 1620, 1503 cm$^{-1}$; NMR (CDCl$_3$) δ 1.17 (C$_6$′-CH$_3$, J=6), 2.82 (C$_4$-NCH$_3$), b 3.28 (OCH$_3$), 4.78 (H$_1$′).

Analysis Calcd. for: C$_{50}$H$_{61}$N$_5$O$_{14}$: C, 62.82; H, 6.43; N, 7.32 Found: C, 62.11; H, 6.47; N, 7.29

EXAMPLE 10

Tetra-N-benzyloxycarbonyl-4-N-D-alanylfortimicin B (34)

To a stirred solution of 2.26 g. of 1,2′,6′-tri-N-benzyloxycarbonylfortimicin B (3), 0.856 g. of N-benzyloxycarbonyl-D-alanine and 0.972 g. of 1-hydroxybenzotriazole monohydrate in 6.0 ml. of tetrahydrofuran, cooled in an ice bath, was added 0.816 g. of N,N′-dicyclohexylcarbodiimide dissolved in 6.0 ml. of tetrahydrofuran. An additional 6.0 ml. of tetrahydrofuran was used to rinse all the N,N′-dicyclohexylcarbodiimide into the reaction vessel. The reaction was stirred for 1 hour at 0° and then for 18 hours at ambient temperature. Insoluble N,N′-dicyclohexylurea was removed by filtration through a sintered glass funnel and the tetrahydrofuran was removed under reduced pressure to give 4.15 g. of a white foam. The product was chromatographed on a column of silica gel prepared and eluted with a solvent system consisting of benzene-methanol-95% ethanol-concentrated ammonium hydroxide (23.5:1.4:2.0:0.2 v/v). Fractions enriched in the desired product were taken to dryness and the residue repeatedly rechromatographed on a column of silica gel prepared and eluted with a solvent system consisting of cyclohexaneacetone (1:1 v/v). Fractions containing pure tetra-N-benzyloxycarbonyl-4-N-D-alanylfortimicin B (34) were pooled and the solvent evaporated to give 0.669 g. of product as a white foam: $[\alpha]_D^{24}+41.4°$ (C 1.0, CH$_3$OH); IR 1710, 1625, 1498 cm$^{-1}$; NMR (CDCl$_3$) δ 1.15 (C$_6$′-CH$_3$, J=6.8), 1.28

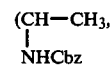

J=6.5), 2.88 (C$_4$-NCH$_3$), 3.27 (OCH$_3$), 4.82 (H$_1$′, J=3.7).

Analysis Calcd. for: C$_{50}$H$_{61}$N$_5$O$_{14}$: C, 62.82; H, 6.43; N, 7.32 Found: C, 62.83; H, 6.59; N, 7.09

EXAMPLE 11

Tetra-N-benzyloxycarbonyl-4-N-L-alanylfortimicin B (35)

To a stirred solution of 2.26 g. of 1,2′,6′-tri-N-benzyloxycarbonylfortimicin B (3), 0.853 g. of N-benzyloxycarbonyl-L-alanine and 0.963 g. of 1-hydroxybenzotriazole monohydrate in 6.0 ml. of tetrahydrofuran, cooled in an icewater bath, was added 0.803 g. of N,N′-dicyclohexylcarbodiimide dissolved in 6.0 ml. of tetrahydrofuran. An additional 6.0 ml. of tetrahydrofuran was used to rinse all the N,N′-dicyclohexylcarbodiimide into the reaction vessel. Stirring at 0° was continued for 1 hour and then at ambient temperature for 18 hours. Insoluble N,N′-dicyclohexylurea was removed by filtration and the filtrate concentrated to dryness to give 4.20 g. of a white foam. The product was chromatographed on a column of silica gel prepared and eluted with a solvent system consisting of benzene-methanol-95% ethanol-concentrated ammonium hydroxide (23.5:1.4:2.0:0.2 v/v). Fractions containing the major portion of the tetra-N-benzyloxycarbonyl-4-N-L-alanylfortimicin B (35) were collected and rechromatographed on a column of silica gel prepared and eluted with a solvent system consisting of acetone-hexane (1:1 v/v). Fractions containing the desired product were collected and passed through a column of Sephadex LH-20 prepared and eluted with 95% ethanol. Fractions containing pure tetra-N-benzyloxycarbonyl-4-N-L-alanylfortimicin B (35) were concentrated to dryness to give 1.29 g. of a colorless foam: $[\alpha]_D^{24}+37.5°$ (C 1.0, CH$_3$OH); IR 1712, 1630, 1500 cm$^{-1}$; NMR (CDCl$_3$) δ 1.17 (C$_6$′-CH$_3$, J=6.5), 1.27

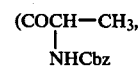

J=7.0), 2.97 (C$_4$-NCH$_3$), 3.29 (OCH$_3$), 4.77 (H$_1$′, J=3.0).

Analysis Calcd. for: C$_{50}$H$_{61}$N$_5$O$_{14}$: C, 62.82; H, 6.43; N, 7.32 Found: C, 62.80; H, 6.58; N, 7.10

EXAMPLE 12

Tetra-N-benzyloxycarbonyl-4-N-L-alanylglycylfortimicin B (36)

To a stirred solution of 1.09 g. of 1,2′,6′-tri-N-benzyloxycarbonylfortimicin B (3), 0.440 g. of N-benzyloxycarbonyl-L-alanylglycine and 0.50 g. of 1-hydroxybenzotriazole monohydrate in 6.0 ml. of tetrahydrofuran was added a solution of 0.416 g. of N,N'-dicyclohexylcarbodiimide in 3.0 ml. of tetrahydrofuran. An additional 3.0 ml. of tetrahydrofuran was used to rinse all the N,N'-dicyclohexylcarbodiimide into the reaction vessel. Stirring was continued for 20 hours at ambient temperature. Insoluble N,N'-dicyclohexylurea was removed by filtration through a sintered glass funnel. The filtrate was concentrated to dryness to give 2.02 of a yellow foam. Pure product was recovered by column chromatography of the reaction mixture on silica gel with a solvent system composed of benzene-methanol-95% ethanol-concentrated ammonium hydroxide (23.5:1.4:2.0:0.2 v/v). Fractions containing the desired product were evaporated to give 1.08 g. of tetra-N-benzyloxycarbonyl-4-N-L-alanylglycylfortimicin B (36): $[\alpha]_D^{24}+30.0°$ (C 1.02, $CH_3OH$); IR 1711, 1640, 1500 $cm^{-1}$; NMR ($CDCl_3$) δ 1.17 ($C_6'$-$CH_3$), 1.29

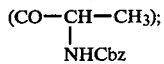

2.85 ($C_4$-$NCH_3$), 3.30 ($OCH_3$).

Analysis Calcd. for: $C_{52}H_{64}N_6O_{15}$: C, 61.35; H, 6.37; N, 8.30 Found: C, 61.68; H, 6.52; N, 8.28

EXAMPLE 13

Tetra-N-benzyloxycarbonyl-4-N-L-histidylfortimicin B (37)

A solution of 1.50 g. of 1,2',6'-tri-N-benzyloxycarbonylfortimicin B (3) in 5 ml. of ethyl acetate was cooled in an acetone-Dry Ice bath and a cold solution of N-benzyloxycarbonyl-L-histidylazide in 19 ml. of ethyl acetate, prepared from 1.21 g. of N-benzyloxycarbonyl-L-histidylhydrazide according to F. Schneider [Z. Physiol. Chem., 320, 82 (1960)] was added with stirring. The reaction mixture was stirred at −15° for 40 minutes, then at 4"C. for 24 hours, and finally at room temperature overnight. Two drops of a concentrated ammonium hydroxide solution was evaporated under reduced pressure at room temperature to leave a residue of 2.36 g. of crude reaction product. The latter was chromatographed on 180 g. of silica gel using methylene chloride-95 aqueous methanol-concentrated ammonium hydroxide (1170:70:5 v/v) as the eluating solvent. The early chromatographic fractions contained nonpolar substances together with unreacted 1,2',6'-tri-N-benzyloxycarbonylfortimicin B (0.35 g.). The residue obtained from the next group of fractions contained a small amount of starting material together with the desired tetra-N-benzyloxycarbonyl-4-N-histidylfortimicin B (37, 1.02 g.). Later fractions contained 0.30 g. of pure tetra-N-benzyloxycarbonyl-4-N-L-histidylfortimicin B (37).

The mixture described above (1.02 g.) containing starting material and the desired product was rechromatographed on 140 g. of silica gel using benzene-methanol-95% ethanol (1174:34:136 v/v) as the eluent. Evaporation of the combined fractions containing tetra-N-benzyloxycarbonyl-4-N-histidylfortimicin B (37) afforded a residue of 0.75 g. of 37.

A part of the above substance was purified for analysis by chromatography on a Sephadex LH-20 column using 95% ethanol as the eluent. The fractions containing the desired compound were combined, evaporated and the residue was dissolved in chloroform. The chloroform solution was washed with water. The aqueous layer was separated, the organic solution was filtered through a sintered glass funnel and evaporated. The residue was pure by TLC: $[\alpha]_D^{22}+32°$ (C 1.01, $CHCl_3$); IR (KBr-pellet) 1710, 1631, 1505 $cm^{-1}$; NMR ($CDCl_3$) δ 1.15 (6'-$CH_3$); 2.91, 2.93 ($C_4$-$N$-$CH_3$); 3.22, 3.29 ($OCH_3$); 5.03, 5.07 (Cbz-$CH_2$); 7.1-7.4 (Cbz-Arom).

Analysis Calcd. for: $C_{53}H_{63}N_7O_{14}$: C, 62.28; H, 6.21; N, 9.59 Found: C, 62.05; H, 6.31; N, 9.44

EXAMPLE 14

Tetra-N-benzyloxycarbonyl-4-N-(DL-2-hydroxy-3-aminopropionyl)-fortimicin B (38)

The N-hydroxy-5-norbornene-2,3-dicarboximide active ester of N-benzyloxycarbonyl-DL-2-hydroxy-3-aminopropionic acid was prepared according to the general procedure described by M. Fujino, et al [Chem. Pharm. Bull. Japan, 22, 1857 (1974)]. The N-Benzyloxycarbonyl-DL-2-hydroxy-3-aminopropionic acid (1.44 g.) was allowed to react with 1.11 g. of N-hydroxy-5-norbornene-2,3-dicarboximide in the presence of 1.28 g. of N,N-dicyclohexylcarbodiimide in 10 ml. of tetrahydrofuran-dioxane (1:1 v/v) solution. The N,N'-dicyclohexylurea which was formed in the course of the above reaction was collected on a filter and the active ester solution was added to a flask containing 2.25 g. of 1,2',6'-tri-N-benzyloxycarbonylfortimicin B (3). The resulting mixture was then stirred at room temperature for 2 days. A small amount of N,N'-dicyclohexylurea was collected on a filter and the filtrate was evaporated under reduced pressure to afford a residue of 5.46 g. The substance was chromatographed on 270 g. of silica gel with benzene-methanol-95% ethanol-concentrated ammonium hydroxide (1174:34:136:10 v/v). The early chromatographic fractions contained 1.82 g. of the desired product contaminated by a small amount of a less polar impurity as shown by TLC. The mixture was rechromatographed on 180 g. of silica gel using benzene-methanol (85:15 v/v) as the eluent. Evaporation of the appropriate fractions yielded 1.08 g. of the desired tetra-N-benzyloxycarbonyl-4-N-(DL-2-hydroxy-3-aminopropionyl) fortimicin B (38).

An analytical sample was prepared by chromatography on a Sephadex LH-20 column. The product obtained was a mixture of the D- and L- epimers as shown by TLC and NMR: $[\alpha]_D^{23}+42°$ (C 1.07, $CH_3OH$); IR ($CDCl_3$); 1705, 1628, 1500 $cm^{-1}$; NMR ($CDCl_3$) δ 3.03 ($C_4$-$NCH_3$); 3.36, 3.31 ($OCH_3$); 5.0-5.1 (Cbz-CH); 7.2-7.4 (Cbz-Arom).

Analysis Calcd. for: $C_{50}H_{61}N_5O_{15}$: C, 61.78; H, 6.33; N, 7.20 Found: C, 61.71; H, 6.58; N, 7.27

The epimers could be separated by chromatography on a Sephadex LH-20 column using chloroform-hexane (1:1 v/v) as the eluent. In this manner, the tetra-N-benzyloxycarbonyl-4-N-(C-2-hydroxy-3-aminopropionyl)-fortimicin B as well as the tetra-N-benzyloxycarbonyl-4-N-(L-2-hydroxy-3-aminopropionyl) fortimicin B could be obtained in pure form.

EXAMPLE 15

Tetra-N-benzyloxycarbonyl-4-N-L-leucylglycylfortimicin B (39)

A solution of the N-hydroxy-5-norbornene-2,3-dicarboximide active ester of N-benzyloxycarbonyl-L-leucylglycine was prepared according to the general procedure of M. Fujino, et al [Chem. Pharm. Bull. Japan, 22, 1857 (1974)]. A solution of 1.27 g. of N-benzyloxycarbonylleucylglycine and 0.72 g. of N-hydroxy-5-norbornene-2,3-dicarboximide in 5 ml. of tetrahydrofuran was cooled in an ice bath and 0.83 g. of N,N'-dicyclohexylcarbodiimide was added to the cold solution together with 1 ml. of tetrahydrofuran. The reaction mixture was stirred at low temperature for 40 minutes and then at room temperature for 2½ hours. The N,N'-dicyclohexylurea formed during the reaction was collected on a filter and washed with three 1-ml. portions of tetrahydrofuran.

The solution of the active ester obtained above was allowed to react with 1.50 g. of 1,2',6'-tri-N-benzyloxycarbonylfortimicin B (3) for 20 hours with stirring at room temperature. Evaporation of the solvent yielded a residue of 3.59 g. which was chromatographed on 280 g. of silica gel using benzene-methanol-95% ethanol-ammonium hydroxide (1174:34:136:10 v/v) as the eluent. A total of 1.76 g. of pure tetra-N-benzyloxycarbonyl-4-N-L-leucylglycylfortimicin B (39) was obtained after evaporation of the solvent from the appropriate fractions.

A part of the product described above was prepared for analysis by chromatography on a Sephadex LH-20: $[\alpha]_D^{27}+24°$ (C 1.08, CHCl$_3$); IR (KBr-pellet) 1710, 1636, 1500 cm$^{-1}$; NMR (CDCl$_3$) $\delta$ 0.92 (Leu-CH$_3$); 1.17 (C$_6$'-CH$_3$, J=6.0), 2.82 (C$_4$-NCH$_3$), 3.30 (OCH$_3$), 5.0–5.1 (Cbz-CH$_2$), 7.2–7.4 (Cbz-Arom).

Analysis Calcd. for: C$_{55}$H$_{70}$N$_6$O$_{15}$: C, 62.60; H, 6.69; N, 7.96 Found: C, 62.31; H, 6.78; N, 7.93

EXAMPLE 16

4-N-(N-tert-butyloxycarbonylglycyl)-1,2',6'-tri-N-benzyloxycarbonylfortimicin B (40)

The N-hydroxy-5-norbornene-2,3-dicarboximide active ester of N-tert-butyloxycarbonylglycine was prepared according to the general procedure of M. Fujino et al [Chem. Pharm. Bull. Japan, 22 1857 (1974)]. In this case the active ester was isolated and recrystallized from ethyl acetate-heptane, m.p. 126°–128°.

A solution prepared from 3.01 g. of 1,2',6'-tri-N-benzyloxycarbonylfortimicin B (3) and 3.03 g. of the above prepared active ester in 10 ml. of chloroform was initially cooled by immersion in an ice bath. The mixture was then stirred overnight at room temperature. Evaporation of the solvent left a residue of 6.84 g. of the crude coupling product which was purified by chromatography on 270 g. of silica gel using benzene-methanol-95% ethanol-concentrated ammonium hydroxide (1174:34:136:10 v/v) as the eluent. The early chromatographic fractions contained 4-N-(N-tert-butyloxycarbonylglycyl)-1,2',6'-tri-N-benzyloxycarbonylfortimicin B (40) contaminated by a small amount of a more polar higher substituted compound. Evaporation of the solvent yielded a residue of 3.07 g. of a mixture. From the later fractions, 0.49 g. of unreacted 1,2',6'-tri-N-benzyloxycarbonylfortimicin B (3) was obtained after evaporation of the solvent. Repeated rechromatography of the mixture (3.07 g.) containing the desired product on silica gel in benzene-methanol 85:15 followed by Sephadex LH-20 chromatography using 95% ethanol as the eluent afforded 1.07 g. of pure 4-N-(N-tert-butyloxycarbonyl)glycyl-1,2',6'-tri-N-benzyloxycarbonylfortimicin B (40): $[\alpha]_D^{26}+36°$ (C 1.05, CHCl$_3$); IR (Kbr disc) 1712, 1640, 1500 cm$^{-1}$; NMR (CDCl$_3$) $\delta$ 1.44 (tert-butyloxy-CH$_3$), 2.82 (C$_4$-NCH$_3$), 3.30 (OCH$_3$); 5.0–5.1 (Cbz-CH$_2$), 7.2–7.4 (Cbz-Arom).

Analysis Calcd. for: C$_{46}$H$_{61}$N$_5$O$_{14}$: C, 60.84; H, 6.77; N, 7.71 Found: C, 60.52; H, 6.99; N, 7.66

The above mentioned more polar substances contaminating the desired product in the early chromatographic fractions was di-/4-N, 5-0 (or 2-0)-tert-butyloxycarbonylglycyl/-1,2',6'-tri-N-benzyloxycarbonylfortimicin B. Purification of this substance provided an analytical sample: $[\alpha]_D^{22}+37°$ (C 1.01, CHCl$_3$); IR (KBr-disc) 1710, 1648, 1505 cm$^{-1}$; NMR (CDCl$_3$) $\delta$ 4.9–5.1 (Cbz-CH$_2$), 7.1–7.4 (Cbz-Arom).

Analysis Calcd. for: C$_{53}$H$_{72}$N$_6$O$_{17}$: C, 59.76; H, 6.81; N, 7.89 Found: C, 59.63; H, 7.04; N, 7.86

EXAMPLE 17

4-N-Glycyl1,2',6'-tri-N-benzyloxycarbonylfortimicin B trifluoroacetate salt (41)

A solution of 0.78 g. of 4-N-(N-tert-butyloxycarbonylglycyl)-1,2',6'-tri-N-benzyloxycarbonylfortimicin B (40) in 5 ml. of methylene chloride and 5 ml. of trifluoroacetic acid was stirred at room temperature for 20 minutes. The solution was evaporated under reduced pressure and the residue was redissolved in 15 ml. of methylene chloride and likewise evaporated. The last process was repeated six times. The partially deprotected substance was dried over potassium hydroxide pellets and phosphorous pentoxide under high vacuum for several hours. The residue of 1.06 g. of 4-N-glycyl-1,2',6'-tri-N-benzyloxycarbonylfortimicin B trifluoroacetate salt (41) still contained adhering trifluoroacetic acid in excess of that expected for the salt.

EXAMPLE 18

Tetra-N-benzyloxycarbonyl-4-N-(DL-2-hydroxy-4-aminobutyryl)glycylfortimicin B (42)

The N-hydroxy-5-norbornene-2,3-dicarboximide active ester of N-benzyloxycarbonyl DL-2-hydroxy-4-aminoburyric acid was prepared according to the procedure of M. Fujino, et al [Chem. Pharm. Bull. Japan, 22, 1857 (1974)]. To an ice cold solution of 0.40 g. of N-benzyloxycarbonyl-DL-2-hydroxy-4-aminoburyric acid and 0.32 g. of N-hydroxy-5-norbornene-2,3-dicarboximide in 3 ml. of tetrahydrofuran-dioxane (1:1 v/v), there was added, with stirring, 0.36 g. of N,N'-dicyclohexylcarbodiimide and 1 ml. of the above solvent mixture. The solution was stirred in the cold for 30 minutes and then at room temperature for 2 hours. The N,N'-dicyclohexylurea which formed in the above reaction was collected on a filter and washed with three 1-ml. portions of tetrahydrofuran-dioxane (1:1 v/v).

The filtrate containing the active ester was collected in a flask containing 4-N-glycyl-1,2',6'-tri-N-benzuloxycarbonylfortimicin B trifluoroacetate salt (41) and the reaction mixture was immersed into an ice-salt bath. Then 0.56 ml. of triethylamine was added to the mixture to neutralize the trifluoroacetic acid. The reaction mixture was stirred overnight at room temperature. An additional 0.3 ml. of triethylamine was added and stirring at room temperature was continued for 30 minutes. A small amount of solid was collected on a filter and washed with several small portions of tetrahydrofuran-dioxane (1:1 v/v). Evaporation of the filtrate provided a residue of 2.37 g. which was chromatographed on 180 g. of silica gel with benzene-methanol-95% ethanol-concentrated ammonium hydroxide (1174:34:136:10 v/v) as the eluent to yield 0.35 g. of product. This substance was rechromatographed on a Sephadex LH-20 column in a 95% ethanol solution. The tetra-N-benzyloxycarbonyl-4-N-(DL-2-hydroxy-4-aminobutyryl)-glycylfortimicin B (42) had the following physical constants: $[\alpha]_D^{25}+29°$ (C 1.01, CHCl$_3$); IR (KBr-disc) 1710, 1638, 1510 cm$^{-1}$; NMR (CDCl$_3$) δ 2.90, 2.99 (NCH$_3$), 3.32 (OCH$_3$); 5.0–5.1 (Cbz-CH$_2$); 7.2–7.4 (Cbz-Arom).

Analysis Calcd. for: C$_{53}$H$_{66}$N$_6$O$_{16}$: C, 61.02; H, 6.38; N, 8.06 Found: C, 60.80; H, 6.44; N, 8.02

EXAMPLE 19

Tetra-N-benzyloxycarbonylglycylglycylglycylglycylfortimicin B (43)

The N-hydroxy-5-norbornene-2,3-dicarboximide active ester of N-benzyloxycarbonylglycylglycine was prepared according to the procedure of M. Fujino, et al [Chem. Pharm. Bull. Japan, 22, 1857 (1974)]. To an ice-cold solution of 0.38 g. of N-benzyloxycarbonylglycylglycine and 0.27 g. of N-hydroxy-5-norbornene-2,3-dicarboximide in 4 ml. of N,N'-dimethylformamide there was added, with stirring, 0.31 g. of N,N'-dicyclohexylcarbodiimide and 1 ml. of N,N'-dimethylformamide. The mixture was stirred in the cold for 1 hour and at room temperature for 3 hours. The N,N'-dicyclohexylurea was collected on a filter and washed with three 1-ml. portions of N,N'-dimethylformamide.

The filtrate containing the active ester was collected in a flask containing the 4-N-glycyl-1,2',6'-tri-N-benzyloxycarbonylfortimicin B trifluoroacetate salt (41) freshly prepared from 0.91 g. of 4-N-(N-tert-butyloxycarbonylglycyl)-1,2',6'-tri-N-benzyloxycarbonylfortimicin B (40) according to the procedure described above in Example 17. The reaction mixture was cooled in an ice bath and 0.52 ml. of triethylamine was added to the cold solution to neutralize the trifluoroacetic acid. The reaction mixture was stirred at room temperature overnight. Evaporation of the solvent yielded a residue of 2.04 g. The substance was purified by chromatography on 180 g. of silica gel using benzene-methanol-95% ethanol-concentrated ammonium hydroxide (1174:34:136:10 v/v) as the eluent. Evaporation of the appropriate chromatographic fractions left a residue of 0.90 g. of the desired tetra-N-benzyloxycarbonyl-4-N-glycylglycylglycylfortimicin B (43): $[\alpha]_D^{23}+44°$ (C 1.01, CHCl$_3$); IR (CDCl$_3$) 1705, 1670, 1505 cm$^{-1}$; NMR (CDCl$_3$) δ 2.95 (C$_4$-NCH$_3$): 3.33 (OCH$_3$); 5.0–5.1 (Cbz-CH$_2$); 7.2–7.4 (Cbz-Arom).

Analysis Calcd. for: C$_{53}$H$_{65}$N$_7$O$_{16}$: C, 60.27; H, 6.20; N, 9.28 Found: C, 60.09; H, 6.22; N, 9.14

EXAMPLE 20

Tetra-N-benzyloxycarbonyl-4-N-(DL-2-hydroxy-3-aminopropionyl)glycylfortimicin B (44)

To an ice-cold stirred solution of 4-N-glycyl-1,2',6'-tri-N-benzyloxycarbonylfortimicin B trifluoroacetate salt, prepared from 0.82 g. of 4-N-(N-tert-butyloxycarbonylglycyl)-1,2',6'-tri-N-benzyloxycarbonylfortimicin B according to the procedure described in Example 17, and the N-hydroxy-5-norbornene-2,3-dicarboximide active ester, prepared from 0.32 g. of N-benzyloxycarbonyl-DL-2-hydroxy-3-aminopropionic acid as described in Example 14, in 7 ml. of tetrahydrofuran-dioxane (1:1 v/v) there was added 0.4 ml. of triethylamine. The mixture was stirred in the cold for 40 minutes and then overnight at room temperature. The solvent was evaporated to leave a residue of 2.16 g. The residue was purified by chromatography on 180 g. of silica gel using benzene-methanol-95% ethanol-concentrated ammonium hydroxide (1174:34:136:10 v/v) as the eluent. Evaporation of the appropriate fractions led to the isolation of 0.83 g. of product. The latter was chromatographed on a Sephadex LH-20 column using 95% ethanol as the eluent. A total of 0.74 g. of pure tetra-N-benzyloxycarbonyl-4-N-(DL-2-hydroxy-3-aminopropionyl)glycylfortimicin B was obtained (44). An analytical sample had the following physical constants: $[\alpha]_D^{23}+32°$ (C 1.00, CHCl$_3$); IR (CDCl$_3$) 1705, 1636, 1503 cm$^{-1}$; NMR (CDCl$_3$) δ 2.90, 2.96 (C$_4$-NCH$_3$); 3.31 (OCH$_3$) 5.0–5.1 (Cbz-CH$_2$), 7.2–7.4 (Cbz-Arom).

Analysis Calcd. for: C$_{52}$H$_{64}$N$_6$O$_{16}$: C, 60.68; H, 6.27; N, 8.17 Found: C, 60.86; H, 7.47; N, 8.20

The procedure for removal of the protecting benzyloxycarbonyl groups

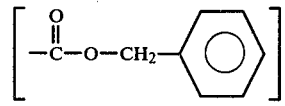

from the per-N-carbobenzyloxycarbonyl derivatives, is as illustrated in Example 21 below, by the conversion of tetra-N-benzyloxycarbonyl-4-N-sarcosylfortimicin B (30) to 4-N-sarcosylfortimicin B (13) which is isolated as the tetrahydrochloride salt.

EXAMPLE 21

4-N-Sarcosylfortimicin B (13)

Tetra-N-benzyloxycarbonyl-4-N-sarcosylfortimicin B (30, 0.840 g.) hydrogenolyzed in 150 ml. of 0.2 N hydrochloric acid in methanol (the 0.2 N hydrochloric acid solution was prepared by diluting 16.8 ml. of concentrated hydrochloric acid to 1000 ml. with methanol) for 4 hours under 3 atmospheres of hydrogen in the presence of 0.800 g. of 5% palladium on carbon. The catalyst was removed by filtration and the methanol was evaporated under reduced pressure. Residual water and excess acid was removed by co-distillation with methanol under reduced pressure to yield 0.512 g. of 4-N-sarcosylfortimicin B (13) as the tetrahydrochloride salt: $[\alpha]_D^{20}+81.3°$ (C 1.0, CH$_3$OH); IR (KBr disc) 1640 cm$^{-1}$; NMR (D$_2$O) δ 1.84 (C$_6$'-CH$_3$, J=6.6), 3.32 (COCH$_2$-NCH$_3$), 3.62 (C$_4$-NCH$_3$), 3.99 (OCH$_3$), 5.82 (H$_1$', J=3.2).

Mass Spectrum: M$^+$. Calcd. for C$_{18}$H$_{37}$N$_5$O$_6$ 419.2744 Observed: 419.2732

EXAMPLES 22–37

By the procedure of Example 21 above, using the appropriate N-benzyloxycarbonyl protected intermediates (26, 27, 28, 29, 31, 32, 33, 34, 35, 36, 39, 42, 37, 43, 44, 38), respectively, described above, the following perhydrochloride salts were prepared:

(9) Fortimicin A tetrahydrochloride,
(10) 4-N-(DL-2-Hydroxy-4-aminobutyryl)fortimicin B tetrahydrochloride,
(11) 4-N-Acetylfortimicin B trihydrochloride,
(12) 4-N-Glycylglycylfortimicin B tetrahydorchloride,
(14) 4-N-L-Phenylalanylglycylfortimicin B tetrahydrochloride,
(15) 4-N-(N,N-Dimethylglycyl)fortimicin B tetrahydrochloride,
(16) 4-N-β-Alanylfortimicin B tetrahydrochloride,
(17) 4-N-D-Alanylfortimicin B tetrahydrochloride,
(18) 4-N-L-Alanylfortimicin B tetrahydrochloride,

(19) 4-N-L-Alanylglycylfortimicin B tetrahydrochloride,
(20) 4-N-L-Leucylglycylfortimicin B tetrahydrochloride,
(21) 4-N-(DL-2-Hydroxy-4-aminobutyrl)glycylfortimicin B tetrahydrochloride,
(22) 4-N-Histidylfortimicin B pentahydrochloride,
(23) 4-N-Glycylglycylglycylfortimicin B tetrahydrochloride,
(24) 4-N-(DL-2-Hydroxy-3-aminopropionyl)glycylfortimicin B tetrahydrochloride, and
(25) 4-N-(DL-2-Hydroxy-3-aminopropionyl) fortimicin B tetrahydrochloride.

The characteristic physical data of these compounds is listed in Table I.

TABLE I

| Compound | Rotation (Methanol) | IR (cm$^{-1}$) | Mass Spectra$^{(a)}$ | NMR$^{(b)}$ D$_2$O, δ |
|---|---|---|---|---|
| 9 | $[\alpha]_D^{23} + 82.3°$ (C 1.0) | 1643 | M$^{+\cdot}$ Calcd: 405.2587 Meas: 405.2617 | 1.79(C$_6'$—CH$_3$, J = 7.0), 3.57 (C$_4$—NCH$_3$), 3.93 (OCH$_3$), 5.76 (H$_1'$, J = 3.2) |
| 10 | — | 1600 | M$^{+\cdot}$—H$_2$O Calcd: 431.2744 Meas: 431.2762 | 1.80 (C$_6'$—CH$_3$, J = 6.5) 3.32, 3.64 (C$_4$—NCH$_3$) 3.94, 4.00 (OCH$_3$), 5.78, 5.93 (H$_1'$, J = 3.8, J = 3.6 |
| 11 | $[\alpha]_D^{25} + 87.2$ (C 1.04) | 1600 | M$^{+\cdot}$ Calcd: 391.2556 Meas: 391.2553 | 1.80(C$_6'$—CH$_3$, J = 6.9), 2.62 (COCH$_3$), 3.61 (C$_4$—NCH$_3$), 3.94 (OCH$_3$), 5.77 (H$_1'$, J = 3.2) |
| 12 | $[\alpha]_D^{25} + 70.5°$ (C 1.02) | 1678 | M$^{+\cdot}$ Calcd: 444.2676 Meas: 444.2699 | 1.81(C$_6'$—CH$_3$, J = 6.4), 3.62 (C$_4$—NCH$_3$), 3.95 (OCH$_3$), 5.79 (H$_1'$, J = 3.5) |
| 14 | $[\alpha]_D^{25} + 76.0°$ (C 1.06) | 1674 | M$^{+\cdot}$ Calcd: 553.3350 Meas: 553.3329 | 1.80(C$_6'$—CH$_3$, J = 6.8), 3.59 (C$_4$—NCH$_3$), 3.94 (OCH$_3$), 5.77 (H$_1'$, J = 3.5) 7.85 (—⬡ multiplet)  |
| 15 | $[\alpha]_D^{25} + 79.3°$ (C 1.0) | 1640 | M$^{+\cdot}$ Calcd: 433.2900 Meas: 433.2903 | 1.81(C$_6'$—CH$_3$, J = 6.4), 3.44, 3.47 [N(CH$_3$)$_2$], 3.56 (C$_4$—NCH$_3$), 3.95 (OCH$_3$), 5.80 (H$_1'$, J = 3.0) |
| 16 | $[\alpha]_D^{23} + 61.3°$ (C 1.0) | 1610 | M$^{+\cdot}$ Calcd: 419.2744 Meas: 419.2727 | 1.81(C$_6'$—CH$_3$, J = 6.9), 3.61 (C$_4$—NCH$_3$)3.96 (OCH$_3$), 5.79 (H$_1'$, J = 3.0) |
| 17 | $[\alpha]_D^{20} + 83.2°$ (C 1.0) | 1632 | M$^{+\cdot}$ Calcd: 419.2744 Meas: 419.2723 | 1.81(C$_6'$—CH$_3$, J = 7.0), 2.01 (CO—CHNH$_2$CH$_3$, J = 6.9), 3.69 (C$_4$—NCH$_3$), 3.94 (OCH$_3$), 5.77 (H$_1'$, J = 3.7) |
| 18 | $[\alpha]_D^{20} + 85.2°$(C 1.02) | 1640 | M$^{+\cdot}$ Calcd: 419.2744 Meas: 419.2723 | 1.81(C$_6'$—CH$_3$, J = 7.0), 1.97 (CO—CHNH$_2$CH$_3$, J = 7.0), 3.69 (C$_4$—NCH$_3$), 3.95 (OCH$_3$), 5.80 (H$_1'$, J = 3.8) |
| 19 | $[\alpha]_D^{25} + 76.9°$ (C 1.0) | 1674 | M$^{+\cdot}$ Calcd: 476.2958 Meas: 476.2951 | 1.81(C$_6'$—CH$_3$, J = 6.5), .04 (CO—CHNH$_2$CH$_3$, J = 7.2), 3.63 (C$_4$NCH$_3$), 3.95 (OCH$_3$), 5.78 (H$_1'$, J = 3.2) |
| 20 | $[\alpha]_D^{26} + 62°$ (C 1.00) | 1670, 1630, 1487 | M$^{+\cdot}$ Calcd: 518.3428 Meas: 518.3454 | 1.45 (Leu—CH$_3$, J = 5.0), 1.81 (C$_6'$—CH$_3$, J = 6.5), 3.63 (C$_4$—NCH$_3$), 3.96 (OCH$_3$), 5.79 (H$_1'$, J = 3.5) |
| 21 | $[\alpha]_D^{24} + 58°$ (C 1.01) | 1625, 1485 | M$^{+\cdot}$—3H$_2$O Calcd: 452.2747 Meas: 452.2767 | 1.82 (C$_6'$—CH$_3$, J = 6.5), 3.65 (C$_4$—NCH$_3$), 3.97 (OCH$_3$), 5.80 (H$_1'$, J = 3.5) |
| 22 | $[\alpha]_D^{25} + 87°$ (C 0.96) | 1640, 1590, 1490 | M$^{+\cdot}$—H$_2$O Calcd: 467.2856 Meas: 467.2869 | 1.81 (C$_6'$—CH$_3$, J = 6.5 3.61 (C$_4$—NCH$_3$), 3.92 (OCH$_3$), 5.79 (H$_1'$, J = 3.5), 7.96 (His H-5, J = 1.5), 9.22 (His H-2, J = 1.5) |
| 23 | $[\alpha]_D^{25} + 58°$ (C 1.05) | 1635, 1485 | M$^{+\cdot}$—OH Calcd: 502.2989 Meas: 502.2973 | 1.74 (C$_6'$—CH$_3$, J = 6.5), 3.56 (C$_4$—NCH$_3$), 3.89 (OCH$_3$) 5.81 (H$_1'$, J = 3.5) |
| 24 | $[\alpha]_D^{26} + 68°$ (C 1.00) | 1628, 1485 | M$^{+\cdot}$ Calcd: 492.2907 Meas: 492.2921 | 1.82 (C$_6'$—CH$_3$, J = 6.5), 3.65 (C$_4$—NCH$_3$), 3.97 (OCH$_3$) 5.78 (H$_1'$, J = 3.5) |
| 25 | $[\alpha]_D^{27} + 78°$ (C 1.04) | 1625, 1487 | M$^{+\cdot}$—H$_2$O—NH$_3$ Calcd: 400.2322 | 1.83 (C$_6'$—CH$_3$, J = 6.5), 3.75 (C$_4$—NCH$_3$), 3.99 |

TABLE I-continued

| Compound | Rotation (Methanol) | IR (cm$^{-1}$) Mass Spectra[a] | NMR[b] D$_2$O, δ |
|---|---|---|---|
| | | Meas: 400.2330 | (OCH$_3$), 5.82 (H$_1'$, J = 3.5) |

[a] The mass spectra of the HCl salts of the fortimicin analogs appear as those of the free bases because of thermal dissociation to the free bases prior to volatilization in the mass spectrometer.

[b] The 100 MHz NMR-spectra were determined in D$_2$O solution using TMS as an external standard. To convert the chemical shifts reported to the Internal TSP-scale: δ TMS external = δ TSP internal +0.42 ppm.

EXAMPLES 38–53

In Vitro Antibiotic Activities of 4-N-Acylfortimicin B Derivatives

The in vitro antibiotic activities of the following fortimicin B derivatives:

(10) 4-N-(DL-2-Hydroxy-4-aminobutyryl)fortimicin B tetrahydrochloride,
(11) 4-N-Acetylfortimicin B trihydrochloride,
(12) 4-N-Glycylglycylfortimicin B tetrahydrochloride,
(13) 4-N-Sarcosylfortimicin B tetrahydrochloride,
(14) 4-N-L-Phenylalanylglycylfortimicin B tetrahydrochloride,
(15) 4-N-(N,N-Dimethylglycyl)fortimicin B tetrahydrochloride,
(16) 4-N-β-Alanylfortimicin B tetrahydrochloride,
(17) 4-N-D-Alanylfortimicin B tetrahydrochloride,
(18) 4-N-L-Alanyfortimicin B tetrahydrochloride,
(19) 4-N-L-Alanylglycylfortimicin B tetrahydrochloride,
(20) 4-N-L-Leucylglycylfortimicin B tetrahydrochloride,
(21) 4-N-(DL-2-Hydroxy-4-aminobutyryl)glycylfortimicin B tetrahydrochloride,
(22) 4-N-L-Histidylfortimicin B pentahydrochloride,
(23) 4-N-glycylglycylglycylfortimicin B tetrahydrochloride,
(24) 4-N-(DL-2-Hydroxy-3-aminopropionyl)glycylfortimicin B tetrahydrochloride, and
(25) 4-N-(DL-2-Hydroxy-3-aminopropionyl)fortimicin B tetrahydrochloride are listed in Table II, below.

The in vitro antibiotic activities were determined by a two-fold agar dilution method using Meuller-Hinton agar, 10 ml. per Petri dish. The agar was inoculated with one loopful (0.001 ml. loop) of a 1:10 dilution of a 24 hour broth culture of the indicated test organism and incubated at 37° C. for 24 hours. Fortimicin A disulfate salt was used as the control antibiotic. The activities are listed in Table II. Minimum inhibitory concentrations (MIC) are expressed in mcg./ml.

TABLE II

In Vitro Antibiotic Activity of 4-N-Acylfortimicin B Derivatives

| Organism | Fortimicin A | Compounds | |
|---|---|---|---|
| | | (10) | (11) |
| Staphylococcus aureus Smith | 0.78 | 100 | >100 |
| Streptococcus faecalis 10541 | 50 | >100 | >100 |
| Enterobacter aerogenes 13048 | 1.56 | >100 | >100 |
| Escherichia coli Juhl | 3.1 | >100 | >100 |
| Escherichia coli Bl3676 (Resist) | 12.5 | >100 | >100 |
| Klebsiella pneumoniae 10031 | 1.56 | >100 | >100 |
| Klebsiella pneumoniae KY4262 | 6.2 | >100 | >100 |
| Providencia 1577 | 1.56 | >100 | >100 |
| Pseudomonas aeruginosa BMH #10 | 0.78 | 50 | >100 |
| Pseudomonas aeruginosa KY8512 | 6.2 | >100 | >100 |
| Pseudomonas aeruginosa KY8516 | 25 | >100 | >100 |
| Pseudomonas aeruginosa 209 | >100 | >100 | >100 |
| Saimonella typhimurium Ed. #9 | 1.56 | 100 | >100 |
| Serratia marcescens 4003 | 1.56 | 100 | >100 |
| Shigella sonnei 9290 | 6.2 | >100 | >100 |
| Proteus rettgeri U 6333 | 25 | >100 | >100 |
| Proteus vulgaris Abbott JJ | 3.1 | >100 | >100 |
| Proteus mirabilis Fin. #9 | 6.2 | >100 | 100 |
| | | (12) | (13) |
| Staphylococcus aureus Smith | 0.78 | 12.5 | 3.1 |
| Streptococcus faecalis 10541 | 50 | >100 | 100 |
| Enterobacter aerogenes 13048 | 1.56 | 25 | 6.2 |
| Escherichia coli Juhl | 3.1 | 25 | 6.2 |
| Escherichia coli BL3676 (Resist) | 12.5 | 50 | 25 |
| Klebsiella pneumoniae 10031 | 1.56 | 25 | 6.2 |
| Klebsiella pneumoniae KY4262 | 6.2 | 50 | 25 |
| Providencia 1577 | 1.56 | 50 | 25 |
| Pseudomonas aeruginosa BMH #10 | 0.39 | 1.56 | 0.78 |
| Pseudomonas aeruginosa KY8512 | 6.2 | 50 | 25 |
| Pseudomonas aeruginosa KY8516 | 25 | >100 | 50 |
| Pseudomonas aeruginosa 209 | >100 | >100 | >100 |
| Salmonella typhimurium Ed. #9 | | 3.1 | 3.1 |
| Serratia marcescens 4003 | 1.56 | 6.2 | 3.1 |
| Shigella sonnei 9290 | 6.2 | 25 | 6.2 |
| Proteus rettgeri U 6333 | 25 | 100 | 100 |
| Proteus vulgaris Abbott JJ | 3.1 | 25 | 6.2 |
| Proteus mirabilis Fin. #9 | 6.2 | 50 | 12.5 |
| | | (14) | |
| Staphylococcus aureus Smith | 0.78 | >100 | |
| Streptoccoccus faecalis 10541 | 50 | >100 | |
| Enterobacter aerogenes 13048 | 1.56 | >100 | |
| Escherichia coli Juhl | 3.1 | 100 | |
| Escherichia coli BL3676 (Resist) | 12.5 | >100 | |
| Klebsiella pneumoniae 10031 | 1.56 | >100 | |
| Klebsiella pneumoniae KY4262 | 6.2 | >100 | |
| Providencia 1577 | 1.56 | >100 | |
| Pseudomonas aeruginosa BMH #10 | 0.78 | 3.1 | |
| Pseudomonas aeruginosa KY8512 | 6.2 | >100 | |
| Pseudomonas aeruginosa KY8516 | 25 | >100 | |
| Pseudomonas aeruginosa 209 | >100 | >100 | |
| Salmonella typhimurium Ed. #9 | 1.56 | >100 | |
| Serratia marcescens 4003 | 1.56 | 100 | |
| Snigella sonnei 9290 | 6.2 | 50 | |
| Proteus rettgeri U 6333 | 25 | >100 | |
| Proteus vulgaris Abbott JJ | 3.1 | >100 | |
| Proteus mirabilis Fin. #9 | 6.2 | >100 | |
| | | (15) | (16) |
| Staphylococcus aureus Smith | 0.78 | 12.5 | 3.1 |
| Streptococcus faecalis 10541 | 50 | >100 | 100 |
| Enterobacter aerogenes 13048 | 1.56 | >100 | 6.2 |
| Escherichia coli Juhl | 3.1 | 25 | 6.2 |
| Escherichia coli BL3676 (Resist) | 12.5 | >100 | 25 |
| Klebsiella pneumoniae 10031 | 1.56 | >100 | 6.2 |
| Klebsiella pneumoniae KY4262 | 6.2 | >100 | 25 |
| Providencia 1577 | 1.56 | >100 | 25 |
| Pseudomonas aeruginosa BMH #10 | 0.78 | 6.2 | 0.78 |
| Pseudomonas aeruginosa KY8512 | 6.2 | >100 | 25 |
| Pseudomonas aeruginosa KY8516 | 25 | >100 | 50 |
| Pseudomonas aeruginosa 209 | >100 | >100 | >100 |
| Saimonella typhimurium Ed. #9 | 1.56 | 25 | 1.56 |
| Serratia marcescens 40003 | 1.56 | 25 | 1.56 |
| Shigella sonnei 9290 | 6.2 | 50 | 6.2 |
| Proteus rettgeri U 6333 | 25 | >100 | 100 |
| Proteus vulgaris Abbott JJ | 3.1 | 50 | 12.5 |
| Proteus mirabilis Fin. #9 | 6.2 | >100 | 12.5 |
| | | (17) | (18) |
| Staphylococcus aureus Smith | 0.78 | 12.5 | 12.5 |
| Strephtococcus faecalis 10541 | 50 | >100 | >100 |
| Enterobacter aerogenes 13048 | 1.56 | 100 | 25 |
| Escherichia coli Juhl | 3.1 | 100 | 25 |
| Escherichia coli BL3676 (Resist) | 12.5 | >100 | 50 |

TABLE II-continued
In Vitro Antibiotic Activity of 4-N-Acylfortimicin B Derivatives

| Organism | Fortimicin A | Compounds |  |
|---|---|---|---|
| Klebsiella pneumoniae 10031 | 1.56 | >100 | 50 |
| Klebsiella pneumoniae KY4262 | 6.2 | >100 | >100 |
| Providencia 1577 | 1.56 | >100 | 50 |
| Pseudomonas aeruginosa BMH #10 | 0.78 | 100 | 1.56 |
| Pseudomonas aeruginosa KY8512 | 6.2 | 100 | 50 |
| Pseudomonas aeruginosa KY8516 | 25 | >100 | >100 |
| Pseudomonas aeruginosa 209 | >100 | >100 | >100 |
| Salmonella typhimurium Ed. #9 | 1.56 | 50 | 25 |
| Serratia marcescens 4003 | 1.56 | 25 | 6.2 |
| Shigella sonnei 9290 | 6.2 | 50 | 12.5 |
| Proteus rettgeri U 6333 | 25 | >100 | >100 |
| Proteus vulgaris Abbott JJ | 3.1 | 100 | 12.5 |
| Proteus mirabilis Fin. #9 | 6.2 | 50 | 25 |
|  |  | (19) |  |

| Organism | Fortimicin A | Compounds |
|---|---|---|
| Staphylococcus aureus Smith | 0.78 | 50 |
| Streptococcus faecalis 10541 | 50 | >100 |
| Enterobacter aerogenes 13048 | 1.56 | 12.5 |
| Escherichia coli Juhl | 3.1 | 25 |
| Escherichia coli BL3676 (Resist) | 12.5 | >100 |
| Klebsiella pneumoniae 10031 | 1.56 | 50 |
| Klebsiella pneumonaie KY4262 | 6.2 | >100 |
| Providencia 1577 | 1.56 | 12.5 |
| Pseudomonas aeruginosa BMH #10 | 0.78 | 1.56 |
| Pseudomonas aeruginosa KY8512 | 6.2 | 50 |
| Pseudomonas aerguinosa KY8516 | 25 | 100 |
| Pseudomonas aeruginosa 209 | >100 | >100 |
| Salmonella typhimurium Ed. #9 | 1.56 | 6.2 |
| Serratia marcescens 4003 | 1.56 | 6.2 |
| Shigella sonnei 9290 | 6.2 | 12.5 |
| Proteus rettgeri U 6333 | 25 | 50 |
| Proteus vulgaris Abbott JJ | 3.1 | 12.5 |
| Proteus mirabilis Fin. #9 | 6.2 | 25 |
|  |  | (20) |

| Organism | Fortimicin A | Compounds |  |
|---|---|---|---|
| Staphylococcus aureus Smith | 0.78 | 6.2 | 6.2 |
| Streptococcus faecalis 10541 | 50 | >100 | >100 |
| Enterobacter aerogenes 13048 | 3.1 | 50 | 25 |
| Escherichia coli Juhl | 3.1 | 12.5 | 25 |
| Escherichia coli BL3676 (Resist) | 25. | 25 | 100 |
| Klebsiella pneumoniae 10031 | 1.56 | 50 | 25 |
| Klebsiella pneumoniae KY4262 | 6.2 | 50 | 100 |
| Providencia 1577 | 12.5 | >100 | 100 |
| Pseudomonas aeruginosa BMH #10 | 0.39 | 1.56 | 6.2 |
| Pseudomonas aeruginosa KY8512 | 6.2 | 100 | 100 |
| Pseudomonas aeruginosa KY8516 | 12.5 | >100 | >100 |
| Pseudomonas aeruginosa 209 | >100 | >100 | >100 |
| Saimonella typhimurium Ed. #9 | 1.56 | 12.5 | 12.5 |
| Serratia marcescens 4003 | 0.78 | 12.5 | 12.5 |
| Shigella sonnei 9290 | 3.1 | 25 | 50 |
| Proteus rettgeri U 6333 | 25 | 100 | >100 |
| Proteus vulgaris Abbott JJ | 6.2 | 50 | 50 |
| Proteus mirabilis Fin. #9 | 6.2 | >100 | >100 |
|  |  | (21) | (22) |

| Organism | Fortimicin A | Compounds |  |
|---|---|---|---|
| Staphylococcus aureus Smith | 0.78 | 50 |  |
| Streptococcus faecalis 10541 | 50 | >100 |  |
| Enterobacter aerogenes 13048 | 3.1 | >100 |  |
| Escherichia coli Juhl | 3.1 | >100 |  |
| Escherichia coli BL3676 (Resist) | 25 | >100 |  |
| Klebsiella pneumoniae 10031 | 1.56 | >100 |  |
| Klebsiella pneumoniae KY4262 | 6.2 | >100 |  |
| Providencia 1577 | 12.5 | >100 |  |
| Pseudomonas aeruginosa BMH #10 | 0.39 | 50 |  |
| Pseudomonas aeruginosa KY8512 | 6.2 | >100 |  |
| Pseudomonas aeruginosa KY8516 | 12.5 | >100 |  |
| Pseudomonas aeruginosa 209 | >100 | >100 |  |
| Salmonella typhimurium Ed. #9 | 1.56 | >100 |  |
| Serratia marcescens 4003 | 0.78 | >100 |  |
| Shigella sonnei 9290 | 3.1 | >100 |  |
| Proteus rettgeri U 6333 | 25 | >100 |  |
| Proteus vulgaris Abbott JJ | 6.2 | >100 |  |
| Proteus mirabilis Fin. #9 | 6.2 | >100 |  |
|  |  | (23) | (24) |

| Organism | Fortimicin A | Compounds |  |
|---|---|---|---|
| Staphylococcus aureus Smith | 0.78 | 6.2 | 3.1 |
| Streptococcus faecalis 10541 | 50 | >100 | >100 |
| Enterobacter aerogenes 13048 | 3.1 | 25 | 25 |
| Escherichia coli Juhl | 3.1 | 50 | 25 |
| Escherichia coli BL3676 (Resist) | 25 | 100 | 100 |
| Klebsiella pneumoniae 10031 | 1.56 | 50 | 25 |
| Klebsiella pneumoniae KY4262 | 6.2 | >100 | 100 |
| Providencia 1577 | 1.56 | 25 | 25 |
| Pseudomonas aeruginosa BMH #10 | 0.78 | 3.1 | 3.1 |
| Pseudomonas aeruginosa KY8512 | 12.5 | 100 | >100 |
| Pseudomonas aeruginosa KY8516 | 50 | >100 | >100 |
| Pseudomonas aeruginosa 209 | >100 | >100 | >100 |
| Salmonella typhimurium Ed. #9 | 3.1 | 12.5 | 12.5 |
| Serratia marcescens 4003 | 1.56 | 25 | 12.5 |
| Shigella sonnei 9290 | 6.2 | 100 | 50 |
| Proteus rettgeri U 6333 | 25 | >100 | >100 |
| Proteus vulgaris Abbott JJ | 3.1 | 50 | 25 |
| Proteus mirabilis Fin. #9 | 6.2 | >100 | 50 |
|  |  | (25) |  |

| Organism | Fortimicin A | Compounds |
|---|---|---|
| Staphylococcus aureus Smith | 0.78 | 25 |
| Streptococcus faecalis 10541 | 50 | >100 |
| Enterobacter aerogenes 13048 | 3.1 | 50 |
| Escherichia coli Juhl | 3.1 | 50 |
| Escherichia coli BL3676 (Resist) | 25 | >100 |
| Klebsiella pneumoniae 10031 | 1.56 | 50 |
| Klebsiella pneumoniae KY4262 | 6.2 | >100 |
| Providencia 1577 | 1.56 | 100 |
| Pseudomonas aeruginosa BMH #10 | 0.78 | 6.2 |
| Pseudomonas aeruginosa KY8512 | 12.5 | >100 |
| Pseudomonas aeruginosa KY8516 | 50 | >100 |
| Pseudomonas aeruginosa 209 | >100 | >100 |
| Salmonella typhimurium Ed. #9 | 3.1 | 25 |
| Serratia marcescens 4003 | 1.56 | 25 |
| Shigella sonnei 9290 | 6.2 | 50 |
| Proteus rettgeri U 6333 | 25 | >100 |
| Proteus vulgaris Abbott JJ | 3.1 | 50 |
| Proteus mirabilis Fin. #9 | 6.2 | 50 |

The present invention includes within its scope pharmaceutical compositions comprising, as an active ingredient, at least one of the compounds of this invention which exhibit antimicrobial activity in association with the pharmaceutical carrier or diluent. The compounds of this invention can be administered by oral or parenteral routes of administration, i.e., intramuscular, intravenous, or subcutaneous routes of administration, or rectal administration, and can be formulated in dosage forms suitable for each route of administration.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides inert diluents, such compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile water, solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredients in the compositions of this invention may be varied; however, it is necessary that the amount of the active ingredients be such that suitable dosage form is obtained. The selected dosage depends upon the desired therapeutical effect, the route of administration and the duration of treatment desired.

We claim:

1. A compound of the formula

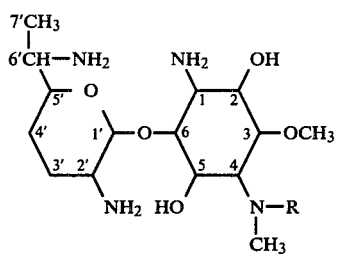

wherein R is acyl, aminoacyl, N-monoloweralkylaminoacyl, N,N-diloweralkylaminoacyl, hydroxy-substituted aminoacyl, or substituted aminoacyl of the formula

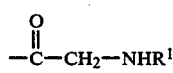

where $R^1$ is an acyl radical derived from an amino acid or a short peptide, and the pharmaceutically acceptable salts thereof.

2. A compound according to claim 1, wherein R is

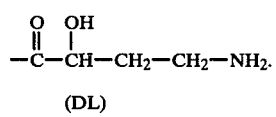
(DL)

3. A compound according to claim 1, wherein R is

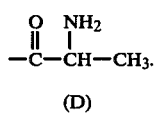
(D)

4. A compound according to claim 1, wherein R is

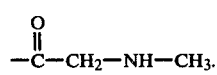

5. A compound according to claim 1, wherein R is

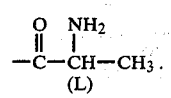
(L)

6. A compound according to claim 1, wherein R is

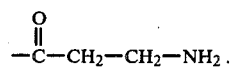

7. A compound according to claim 1, wherein R is

8. A compound according to claim 1, wherein R is

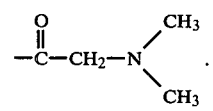

9. A compound according to claim 1, wherein R is

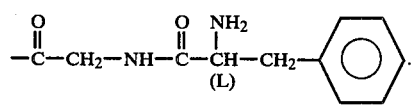
(L)

10. A compound according to claim 1, wherein R is

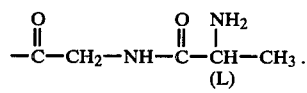
(L)

11. A compound according to claim 1, wherein R is

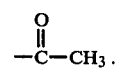

12. A compound according to claim 1, wherein R is

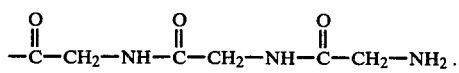

13. A compound according to claim 1, wherein R is

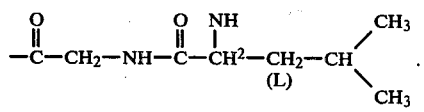
(L)

14. A compound according to claim 1, wherein R is

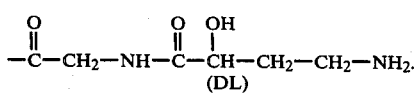
(DL)

15. A compound according to claim 1, wherein R is

16. A compound according to claim 1, wherein R is
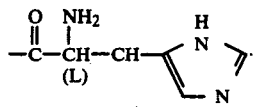
17. A compound according to claim 1, wherein R is
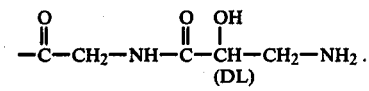
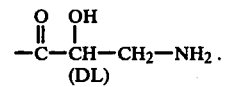
* * * * *